US005120869A

United States Patent [19]

Cartwright

[11] Patent Number: 5,120,869

[45] Date of Patent: Jun. 9, 1992

[54] HERBICIDAL COMPOUNDS

[75] Inventor: David Cartwright, Reading, Great Britain

[73] Assignee: Imperial Chemical Industries plc, London, United Kingdom

[21] Appl. No.: 432,949

[22] Filed: Nov. 7, 1989

[30] Foreign Application Priority Data

Nov. 22, 1988 [GB] United Kingdom ................ 8827262

[51] Int. Cl.[5] .............................................. C07C 69/76

[52] U.S. Cl. ........................................ 560/61; 560/21; 560/43; 560/44; 560/55; 560/62; 562/435; 562/426; 564/164; 564/165; 564/166; 558/389; 558/390; 558/394; 558/397; 568/306; 568/424; 546/296; 546/295; 546/300; 546/302; 546/303

[58] Field of Search ........................ 560/61, 21, 43, 44, 560/55, 62; 564/164, 165, 160; 562/435, 426; 558/389, 390, 394, 397; 568/300, 42.1; 71/107, 108, 111, 112, 105; 546/290, 295, 300, 302, 303; 71/107, 108, 111, 112, 105

[56] References Cited

U.S. PATENT DOCUMENTS 4,419,122 12/1983 Swithenbank .......................... 71/98
4,419,123 12/1983 Swithenbank .......................... 71/98

FOREIGN PATENT DOCUMENTS 003295 8/1979 European Pat. Off. .
034402 8/1981 European Pat. Off. .
0059167 1/1982 European Pat. Off. .
281103 9/1988 European Pat. Off. .

*Primary Examiner*—Paul J. Killos

*Attorney, Agent, or Firm*—Lynn Marcus-Wyner

[57] ABSTRACT

A herbicidal compound of formula (I):

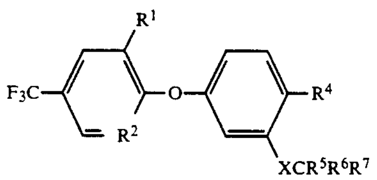

(I)

wherein

X is O, $S(O)_n$ or $NR^a$ where $R^a$ is H or alkyl and n is 0, 1 or 2;
$R^1$ is H or halo;
$R^2$ is N or $CR^3$ where $R^3$ is halo or $NO_2$;
$R^4$ is H, halo, $NO_2$, alkyl, haloalkyl, CN, $CO_2$alkyl, cycloalkyl, phenyl, COalkyl, COphenyl, CHO-,OH, $NH_2$, NHCOalkyl or alkoxy
$R^5$ is H, halo or optionally substituted alkyl;
$R^6$ is H, halo or optionally substituted alkyl; provided that at least one of $R^5$ and $R^6$ is halo;
$R^7$ is CN, CHO, $COOR^8$, $CONR^8R^9$, where $R^8$ is H, optionally substituted alkyl, alkenyl, alkynyl or aryl and $R^9$ is a group $R^8$, $SO_2$alkyl, $NR^{10}R^{11}$ or $N^+R^{10}R^{11}R^{12}$ $Z^-$ where Z is an agriculturally acceptable anion e.g. chloride and $R^{10}$, $R^{11}$ and $R^{12}$ are independently selected from hydrogen and alkyl. Processes for the preparation of these compounds and compositions containing them are also described.

23 Claims, No Drawings

HERBICIDAL COMPOUNDS

This invention relates to diphenyl ether derivatives useful as herbicides and to herbicidal compositions and processes utilizing them.

The compounds have good herbicidal activity.

According to the present invention there is provided a compound of formula (I)

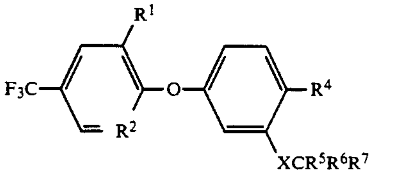

(I)

wherein

X is 0, $S(O)_n$ or $NR^a$ where $R^a$ is H or alkyl and n is 0, 1 or 2;

$R^1$ is H or halo;

$R^2$ is N or $CR^3$ where $R^3$ is halo or $NO_2$;

$R^4$ is H, halo, alkyl, $NO_2$, haloalkyl, CN, $CO_2$alkyl, cycloalkyl, phenyl, COalkyl, COphenyl, CHO, OH, $NH_2$, NHCOalkyl, alkoxy;

$R^5$ is H, halo or optionally substituted alkyl;

$R^6$ is H, halo or optionally substituted alkyl, provided that at least one of $R^5$ or $R^6$ is halo;

$R^7$ is CN, $COOR^8$, CHO, $CONR^8R^9$, where $R^8$ is H, optionally substituted alkyl, alkenyl, alkynyl or aryl and $R^9$ is a group $R^8$, $SO_2$alkyl $NR^{10}R^{11}$ or $N^+R^{10}R^{11}R^{12}$ $Z^-$ where Z is an agriculturally acceptable anion e.q. chloride and $R^{10}$, $R^{11}$ and $R^{12}$ are independently selected from hydrogen and alkyl.

Suitable halo groups for $R^1$ are fluoro and chloro, preferably fluoro.

Suitable groups for $R^2$ are $CR^3$.

Suitable halo groups for $R^3$ are fluoro and chloro, preferably chloro.

Suitable haloalkyl groups for $R^4$ contain from 1 to 6 carbon atoms. A particular example is trifluoromethyl and pentafluoroethyl.

As used herein the term "alkyl" includes straight or branched chains containing up to 10 carbon atoms preferably from 1 to 6 carbon atoms. The terms "alkenyl" and "alkynyl" refer to unsaturated straight or branched chains having from 2 to 10 and preferably from 2 to 6 carbon atoms. The term "aryl" includes phenyl. The term cycloalkyl includes rings containing from 3 to 9 carbon atoms, preferably from 3 to 6 carbon atoms. The term alkoxy includes straight or branched chain containing up to 10 carbon atoms preferably from 1 to 6 carbon atoms.

Examples of optional substituents for alkyl groups $R^5$, $R^6$, $R^8$ and $R^9$, include one or more groups selected from halo such as fluoro, chloro or bromo; nitro; nitrile; aryl such as phenyl; $CO_2R^{13}$, $NHCOR^{13}$ or $NHCH_2CO_2R^{13}$ wherein $R^{13}$ is hydrogen, $C_{1-6}$ alkyl or an agriculturally acceptable cation; $C_{1-6}$ alkoxy; oxo; amino; mono- or di- $C_{1-6}$ alkylamino; $CONR^{14}R^{15}$ wherein $R^{14}$ and $R^{15}$ are independently selected from hydrogen, $C_{1-6}$ alkyl, $C_{2-6}$ alkenyl or $C_{2-6}$ alkynyl or $R^{14}$ and $R^{15}$ are joined together to form a heterocyclic ring having up to 7 ring atoms; and heterocyclyl containing up to 10 ring atoms up to 3 of which may be selected from oxygen, nitrogen and sulphur. An example of a heterocyclic substituent for $R^5$, $R^6$, $R^8$ and $R^9$ is tetrahydrofuranyl. $R^4$ is suitably hydrogen, bromo, chloro, nitro or cyano.

Suitably, $R^5$ and or/ $R^6$ are fluoro. Preferably $CR^5R^6R^7$ is

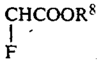

or $CF_2COOR^8$. Preferably $R^8$ is $C_{1-6}$ alkyl.

The structural formula (I) given above is intended to include tautomeric forms of the structure drawn, as well as physically distinguishable modifications of the compounds which may arise, for example, from different ways in which the molecules are arranged in a crystal lattice, or from the inability of parts of the molecule to rotate freely in relation to other parts, or from geometrical isomerism, or from intra-molecular or inter-molecular hydrogen bonding, or otherwise.

Some of the compounds of the invention can exist in enantiomeric forms. The invention includes both enantiomers and mixtures of the two in all proportions.

Particular examples of compounds according to the invention are listed in Table I as well as other salts and zwitterions thereof.

TABLE I

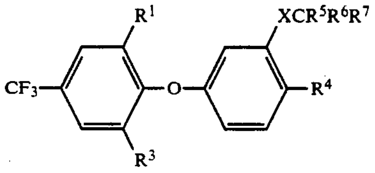

| COMPOUND NO. | $R^1$ | $R^3$ | $R^4$ | $R^5$ | $R^6$ | $R^7$ | X | CHARACTERISING DATA |
|---|---|---|---|---|---|---|---|---|
| 1 | F | Cl | Cl | H | F | $CO_2CH_2CH_3$ | O | n.m.r. 7.6(s, 1H); 7.4 (dd, 1H); 7.35(d, 1H); 6.9(d, 1H); 6.6(dd, 1H); 5.9(d, 1H); 4.4(q, 2H); 1.35(t, 3H). |
| 2 | F | Cl | $NO_2$ | H | F | $CO_2CH_2CH_3$ | O | n.m.r. 8.02(d, 1H); 7.64 (s, 1H); 7.5(dd, 1H); 6.95(d, 1H); 6.75(dd, 1H) 6.0(d, 1H); 4.4(q, 2H); 1.4(t, 3H) |
| 3 | F | Cl | Cl | $CH_3$ | F | $CO_2CH_2CH_3$ | O | n.m.r. 7.6(s, 1H); 7.4 (d, 1H); 7.3(d, 1H); 6.9 |

TABLE I-continued

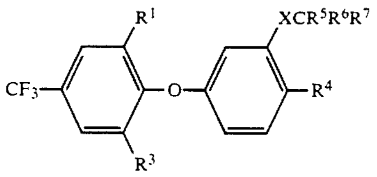

| COMPOUND NO. | $R^1$ | $R^3$ | $R^4$ | $R^5$ | $R^6$ | $R^7$ | X | CHARACTERISING DATA |
|---|---|---|---|---|---|---|---|---|
| | | | | | | | | (d, 1H); 6.6(dd, 1H); 4.2 (q, 2H); 1.85(d, 3H); 1.17(t, 3H) |
| 4 | F | Cl | Br | H | F | $CO_2CH_2CH_3$ | O | n.m.r. 7.6(s, 1H); 7.5 (d, 1H); 7.45(dd, 1H); 6.9(d, 1H); 6.55(dd, 1H); 5.9(d, 1H); 4.35(q, 2H); 1.35(t, 3H) |
| 5 | F | Cl | Cl | H | F | COH | O | m.p. 95-96° C. |
| 6 | F | Cl | Cl | H | F | $CO_2CH_3$ | O | n.m.r. 7.6(s, 1H); 7.43 (dd, 1H); 6.9(d, 1H); 6.6 (dd, 1H); 6.35(d, 1H); 5.95(d, 1H); 3.9(s, 3H). |
| 7 | F | Cl | Cl | H | F | $CO_2(CH_2)_3CH_3$ | O | n.m.r. 7.6(s, 1H); 7.43 (dd, 1H); 7.35(d, 1H); 6.9(d, 1H); 6.6(dd, 1H); 5.9(d, 1H); 4.3(q, 2H); 1.65(m, 2H); 1.4(m, 2H); 0.95(t, 3H). |
| 8 | F | Cl | Cl | F | F | $CO_2CH_2CH_3$ | O | n.m.r. 7.6(s, 1H); 7.4 (dd, 1H); 7.35(d, 1H), 6.95(d, 1H); 6.7(dd, 1H); 4.4(q, 2H); 1.35(t, 3H). |
| 9 | F | Cl | Cl | H | F | $CON(CH_3)_2$ | O | n.m.r. 7.6(s, 1H); 7.4 (dd, 1H); 7.35(d, 1H); 6.9(d, 1H); 6.55(dd, 1H); 6.1(d, 1H); 3.1(d, 6H). |
| 10 | F | Cl | H | H | F | $CO_2CH_2CH_3$ | O | n.m.r. 7.6(s, 1H); 7.4 (d, 1H); 7.3(dd, 1H); 6.9 (d, 1H); 6.7(dd, 2H); 5.9 (d, 1H); 4.35(q, 2H); 1.35 (t, 3H). |
| 11 | H | $NO_2$ | Cl | H | F | $CO_2CH_2CH_3$ | O | n.m.r. 8.25(s, 1H); 7.8 (dd, 1H); 7.48(d, 1H); 7.12 (d, 1H); 7.05(d, 1H); 6.85 5.9(d, 1H); 4.4(q, 2H); 1.35(t, 3H). |
| 12 | H | Cl | Cl | H | F | $CO_2CH_2CH_3$ | O | n.m.r. 7.75(s, 1H); 7.5 (d, 1H); 7.4(d, 1H); 7.05 (d, 1H); 6.95(d, 1H); 6.75(dd, 1H); 5.9(d, 1H); 4.4(q, 2H); 1.35(t, 3H). |
| 13 | Cl | Cl | H | H | F | $CO_2CH_2CH_3$ | O | n.m.r. 7.7(s, 2H); 7.25 (dd, 1H); 6.85(d, 1H); 6.6 (dd, 2H); 5.95(d, 1H); 4.35(q, 2H); 1.35(t, 3H). |
| 14 | F | F | Cl | H | F | $CO_2CH_2CH_3$ | O | n.m.r. 7.35(m, 3H); 6.95 (d, 1H); 6.65(dd, 1H); 5.9(d, 1H); 4.35(q, 2H); 1.35(t, 3H). |
| 15 | Cl | Cl | $NO_2$ | H | F | $CO_2CH_2CH_3$ | O | n.m.r. 8.0(d, 1H); 7.75 (s, 2H); 6.9(d, 1H); 6.65 (dd, 1H); 6.0(d, 1H); 4.36 (q, 2H); 1.37(t, 3H). |
| 16 | Cl | Cl | Cl | H | F | $CO_2CH_2CH_3$ | O | m.p. 110-112° C. |
| 17 | H | Cl | $NO_2$ | H | F | $CO_2CH_2CH_3$ | O | n.m.r. 8.0(d, 1H); 7.85 (s, 1H); 7.65(dd, 1H); 7.25(s, 1H); 6.95(d, 1H); 6.75(dd, 1H); 6.0(d, 1H); 4.35(q, 2H); 1.35(t, 3H). |
| 18 | F | Cl | Cl | H | F | $CO_2CH(CH_3)_2$ | O | n.m.r. 7.6(s, 1H); 7.45 (dd, 2H); 7.35(d, 1H); 6.9 (d, 1H); 6.6(dd, 1H); 5.85 (d, 1H); 5.18(m, 1H); 1.35(t, 6H). |
| 19 | F | Cl | Cl | H | F | $CO_2CH_2CH(CH_3)_2$ | O | n.m.r. 7.6(s, 1H); 7.45 (dd, 1H); 7.35(s, 1H); 6.9(d, 1H); 6.6(dd, 1H); 5.9(d, 1H); 4.1(m, 2H); 2.0(m, 1H); 0.95(d, 6H). |

TABLE I-continued

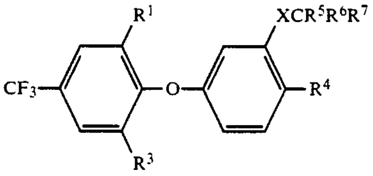

| COMPOUND NO. | $R^1$ | $R^3$ | $R^4$ | $R^5$ | $R^6$ | $R^7$ | X | CHARACTERISING DATA |
|---|---|---|---|---|---|---|---|---|
| 20 | F | Cl | Cl | H | F | 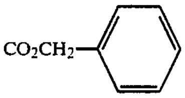 | O | n.m.r. 7.58(s, 1H); 7.35 (m, 7H); 6.88(d, 1H); 6.6 (dd, 1H); 5.95(d, 1H); 5.3 (d, 2H). |
| 21 | F | Cl | Cl | H | F | $CO_2(CH_2)_5CH_3$ | O | n.m.r. 7.6(s, 1H); 7.4 (dd, 1H); 7.35(d, 1H); 6.9(d, 1H); 6.58(dd, 1H); 5.85(d, 1H); 4.3(t, 2H); 1.7(m, 2H); 1.35 (m, 6H); 0.9(t, 3H). |
| 22 | F | Cl | Cl | H | F | $CO_2C(CH_3)_3$ | O | n.m.r. 7.6(s, 1H); 7.42 (dd, 1H); 7.35(d, 1H); 6.9(d, 1H); 6.6(dd, 1H); 5.8(d, 1H); 1.55(s, 9H). |
| 23 | F | Cl | CN | H | F | $CO_2CH_2CH_3$ | O | n.m.r. 7.65(s, 1H); 7.6 (d, 1H); 7.45(dd, 1H); 6.9(d, 1H); 6.65(dd, 1H); 6.0(d, 1H); 4.4(q, 2H); 1.35(t, 3H). |
| 24 | F | Cl | Cl | H | F | $CO_2CH_2C{\equiv}CH$ | O | n.m.r. 7.6(s, 1H); 7.45 (dd, 1H); 7.35(d, 1H); 6.9(s, 1H); 6.6(dd, 1H); 5.95(d, 1H); 4,88(d, 2H); 2.57(s, 1H). |
| 25 | F | Cl | $CH_3$ | H | F | $CO_2CH_2CH_3$ | O | n.m.r. 7.6(s, 1H); 7.4 (d, 1H); 7.1(d, 1H); 6.8 (d, 1H); 6.5(dd, 1H); 5.85 (d, 1H); 4.35(q, 2H); 2.25 (s, 3H); 1.35(t, 3H). |
| 26 | F | Cl | $CO_2CH_3$ | H | F | $CO_2CH_2CH_3$ | O | n.m.r. 7.9(d, 1H); 7.6 (d, 1H); 7.45(q, 1H); 6.85(d, 2H); 6.7(q, 1H); 5.95(d, 2H); 4.4(q, 2H); 3.9(s, 3H); 1.4(t, 3H). |
| 27 | F | Cl | CHO | H | F | $CO_2CH_2CH_3$ | O | n.m.r. 7.9(d, 1H); 7.6 (d, 1H); 7.45(q, 1H); 6.9 (d, 1H); 6.65(q, 1H); 6.05 (d, 1H); 4.4(q, 2H); 1.4 (t, 3H). |
| 28 | F | Cl | ${}_nC_3H_7$ | H | F | $CO_2CH_2CH_3$ | O | n.m.r. 7.6(d, 1H); 7.4 (q, 1H); 7.1(d, 1H); 6.8 (d, 1H); 6.5(q, 1H); 5.9 (d, 1H); 4.4(m, 2H); 2.6 (m, 3H); 1.6(m, 2H); 1.35(t, 3H); 0.9(t, 3H). |
| 29 | F | Cl | 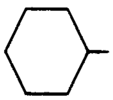 | H | F | $CO_2CH_2CH_3$ | O | n.m.r. 7.5(d, 1H); 7.3 (q, 1H); 7.05(d, 1H); 6.7 (d, 1H); 6.45(q, 1H); 5.8(d, 1H); 4.3(m, 2H); 2.8(m, 1H); 1.7(m, 5H); 1.25(m, 8H). |
| 30 | F | Cl | $COCH_3$ | H | F | $CO_2CH_2CH_3$ | O | n.m.r. 7.85(d, 1H); 7.6 (d, 1H); 7.45(q, 1H); 6.9 (d, 1H); 6.6(q, 1H); 6.05 (d, 1H); 4.4(q, 2H); 2.65 (s, 3H); 1.4(t, 3H). |
| 31 | F | Cl | Cl | H | Br | $CO_2CH_3$ | O | n.m.r. 7.6(s, 1H); 7.45 (d, 1H); 7.35(d, 1H); 6.19(s, 1H); 6.65(d, 1H); 6.45(s, 1H); 3.9(s, 3H). |
| 32 | F | Cl | Cl | H | Br | $CO_2CH_2CH_3$ | O | n.m.r. 7.6(s, 1H); 7.4 (d, 1H); 7.35(d, 1H); 6.9 (s, 1H); 6.65(d, 1H); 6.4 (s, 1H); 4.4(q, 2H); 1.4 (t, 3H). |
| 33 | F | Cl | Cl | H | Cl | $CO_2CH_3$ | O | n.m.r. 7.6(s, 1H); 7.4 |

TABLE I-continued

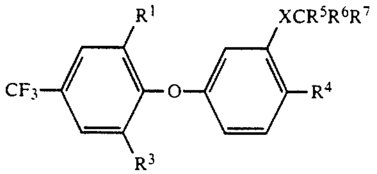

| COMPOUND NO. | $R^1$ | $R^3$ | $R^4$ | $R^5$ | $R^6$ | $R^7$ | X | CHARACTERISING DATA |
|---|---|---|---|---|---|---|---|---|
| | | | | | | | | (d, 1H): 7.35(d, 1H); 6.9 (s, 1H); 6.65(d, 1H); 6.22 (s, 1H); 3.95(s, 3H). |
| 34 | F | Cl | $C_2H_5$ | H | F | $CO_2CH_2CH_3$ | O | n.m.r. 7.6(d, 1H); 7.4 (q, 1H); 7.1(d, 1H); 6.8 (d, 1H); 6.5(q, 1H); 5.9(d, 1H); 4.35(m, 2H); 2.65(q, 2H); 1.35(t, 3H); 1.2(t, 3H). |
| 35 | F | Cl | Cl | H | F | $CONHSO_2CH_3$ | O | |

A further particular example is Compound No. 36

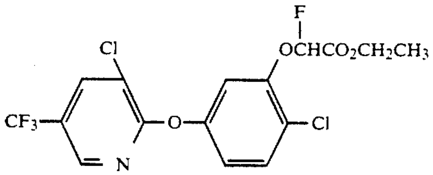

characterising data:

n.m.r. 8.25 (s, 1H); 8.0 (d, 1H); 7.5 (d, 1H); 7.1 (d, 1H); 7.0 (dd, 1H); 5.8-6.05 (d, 1H); 4.4 (g, 2H); 1.4 (t, 3H).

Compounds of formula (I) can be prepared by reaction of a compound of formula (II)

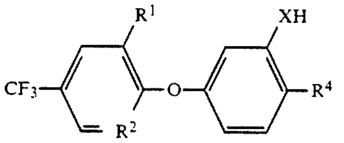

(II)

wherein X, $R^1$, $R^2$ and $R^4$ are as defined in relation to formula (I); with a compound of formula (III)

$$Y—CR^5R^6R^7 \quad (III)$$

wherein $R^5$, $R^6$ and $R^7$ are defined in relation to formula (I) and Y is a leaving group.

Suitably the reaction is carried out in the presence of a base such as sodium hydroxide or potassium carbonate.

Examples of leaving groups for Y include halo such as chloro, bromo or iodo, mesylate or tosylate groups.

The reaction is suitably carried out in an inert organic solvent such as dimethylsulphoxide at a temperature for example of from 40°-120° C. Thereafter if desired one or more of the following steps may be carried out:

i) when $R^7$ is alkoxycarbonyl hydrolysinq to the corresponding acid; and ii) when $R^7$ is COOH esterifying or forming a salt, amide, sulphonamide, hydrazide or hydrazinium derivative.

Compounds of formula (II) may have herbicidal activity in their own right and the use of these compounds as herbicides forms another aspect of the invention. In addition some of the compounds of formula (II) are novel and this forms yet another aspect of the invention. Examples of compounds of formula (II) are shown in Table II.

TABLE II

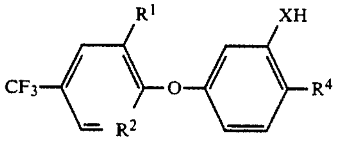

| COMPOUND NO. | $R^1$ | $R^2$ | $R^4$ | X | CHARACTERISING DATA |
|---|---|---|---|---|---|
| 37 | F | C—F | Cl | O | n.m.r. 7.33(d, 2H); 7.27(d, 1H); 6.61 (s, 1H); 6.49(d, 1H); 5.58(s, 1H). |
| 38 | F | C—Cl | Br | O | n.m.r. 7.59(s, 1H); 7.4(d, 2H); 6,55 (s, 1H); 6.45(d, 1H); 5.59(s, 1H). |
| 39 | F | C—Cl | $NO_2$ | O | n.m.r. 8.15(d, 1H); 7.6(s, 1H); 7.45(d, 6.65(d, 1H); 6.45(d, 1H). |
| 40 | F | C—Cl | Cl | O | n.m.r. 7.59(s, 1H); 7.4(dd, 1H); 7.25 (d, 1H); 6.55(d, 1H); 6.46(dd, 1H) 5.62(s, 1H). |
| 41 | Cl | C—Cl | Cl | O | n.m.r. 7.68(s, 1H); 7.26(d, 1H); 6.49 (s, 1H); 6.42(d, 1H); 5.63(s, 1H). |
| 42 | F | C—Cl | H | O | n.m.r. 7.5(s, 1H); 7.3(d, 1H); 7.1(t, 1H 6.5(d, 1H); 6.35(d, 1H); 6.25(d, 4.75(s, 1H). |

TABLE II-continued

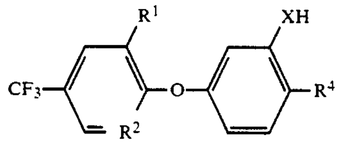

| COMPOUND NO. | $R^1$ | $R^2$ | $R^4$ | X | CHARACTERISING DATA |
|---|---|---|---|---|---|
| 43 | H | C—$NO_2$ | Cl | O | n.m.r. 8.25(s, 1H); 7.75(d, 1H); 7.35 (d, 1H); 7.15(d, 1H); 6.75(s, 1H); 6.6(dd, 1H); 5.95(broad s, 1H). |
| 44 | Cl | C—Cl | $NO_2$ | O | n.m.r. 8.1(d, 1H); 7.75(s, 1H); 6.5 (d, 1H); 6.35(s, 1H). |
| 45 | Cl | C—Cl | H | O | n.m.r. 7.7(s, 1H); 7.15(t, 1H); 6.55(d, 1H) 6.45(d, 1H); 6.35(s, 1H); 4.85 (s, 1H). |
| 46 | F | C—Cl | CN | O | n.m.r. 7.6(s, 1H); 7.45(d, 1H); 7.42(d, 1H) 6.55(d, 1H); 6.5(s, 1H). |
| 47 | F | C—Cl | $CH_3$ | O | n.m.r. 7.55(s. 1H); 7.4(d, 1H); 7.0(d, 1H) 6.4(s, 1H); 6.35(d, 1H); 4.85 (s, 1H); 2.2(s, 3H). |
| 48 | F | C—Cl | $CH_2CH_3$ | O | n.m.r. 7.55(d, 1H); 7.4(q, 1H); 7.0(d, 1H); 6.4(q, 1H & d, 1H); 5.1(s, 1H); 2.6 (q, 2H); 1.2(t, 3H). |
| 49 | F | C—Cl | $CO_2CH_3$ | O | n.m.r. 11.0(s, 1H); 7.85(d, 2H); 7.6(d, 1H); 7.4(dd, 1H); 6.5(dd, 1H); 6.35 (d, 1H); 3.95(s, 3H). |
| 50 | F | C—Cl | CHO | O | n.m.r. 11.4(s, 1H); 9.8(s, 1H); 7.6(d, 1H); 7.55(d, 1H); 7.45(q, 1H); 6.6(q, 1H); 6.3(s, 1H). |
| 51 | F | C—Cl | nPr | O | n.m.r. 7.55(d, 1H); 7.35(q, 1H); 7.0(d, 1H); 6.4(q, 1H & d, 1H); 5.05(s, 1H); 2.5 (t, 2H); 1.6(m, 2H); 0.95(t, 3H). |
| 52 | F | C—Cl | 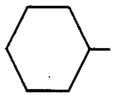 | O | n.m.r. 7.55(d, 1H); 7.35(q, 1H); 7.05(d, 1H) 6.4(d, 1H); 6.35(q, 1H); 5.8(s, 1H); 2.57(m, 1H); 1.85(d, 4H); 1.75 (d, 2H); 1.4(m, 4H). |
| 53 | F | C—Cl | $COCH_3$ | O | n.m.r. 12.6(s, 1H); 7.75(d, 1H); 7.6(d, 1H) 7.45(q, 1H); 6.55(q, 1H); 6.3(d, 1H); 2.6(s, 3H). |
| 54 | Cl | N | Cl | O | n.m.r. 8.3(s, 1H); 8.0(s, 1H); 7.4(d, 1H); 6.9(d, 1H); 6.7(dd, 1H); 5.75 (s, 1H). |
| 55 | F | C—Cl | $C_2F_5$ | O | n.m.r. 10.5(broad 1H); 8.13(d, 1H); 7.5 (d, 1H); 6.77(s, 1H); 6.45(d, 1H). |

Compounds of formula (II) can be prepared by reacting a compound of formula (IV)

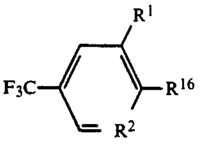

(IV)

wherein $R^1$ and $R^2$ are as defined in relation to formula (I) and $R^{16}$ is halo preferably fluoro or chloro with a compound of formula (V)

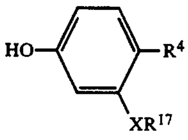

(V)

where X and $R^4$ are as defined in relation to formula (I) and $R^{17}$ is H or a blocking group, preferably alkyl; and thereafter if necessary removing any blocking groups $R^{17}$.

The reaction is preferably carried out in the presence of a base. Suitable bases include potassium carbonate.

The reaction is preferably carried out in an inert organic solvent such as dimethysulphoxide at temperatures for example of from 20°-120° C. optionally. in an inert atmosphere.

Alternatively compounds of formula (I) can be prepared directly by reacting a compound of formula (IV) with a compound of formula (VI)

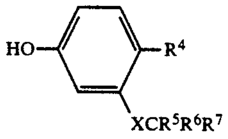

(VI)

wherein X,$R^4$, $R^5$, $R^6$ and $R^7$ are as defined in relation to formula (I). The reaction conditions employed will be similar to these described above for the reaction of compound of formula (IV) with a compound of formula (V). Compounds of formula (I) or (II) where $R^4$ is nitro or halo can be prepared by nitration or halogenation respectively of a compound of formula (VII)

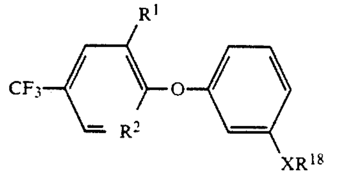

(VII)

wherein $R^1$, $R^2$ and X are as defined in relation to formula (I) and $R^{18}$ is hydrogen or a blocking group such as alkyl, or $CR^5R^6R^7$ where $R^5$, $R^6$ and $R^7$ are as defined in relation to formula (I); and thereafter if necessary removing any blocking groups $R^{18}$ The nitration reaction may be carried out under conventional conditions, for example by reaction with a nitrating agent such as nitric acid in sulphuric acid or copper nitrate and acetic anhydride in acetic acid.

Similarly halogenation may be effected by reation with a halogenating agent such as chlorine or bromine in for example acetic acid. Compounds of formula (VII) can be prepared by reacting a compound of formula (IV) with a compound of formula (VIII)

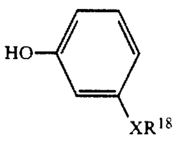

(VIII)

where X is as defined in relation to formula (I) and $R^{18}$ is as defined in relation to formula (VII). The reaction conditions will be similar to those described above for the reaction between a compound of formula (IV) and a compound of formula (V). Removal of blocking groups $R^{17}$ and $R^{18}$ can be effected by reaction with an acid such as hydrobromic acid in acetic acid or with pyridine hydrochloride or boron tribromide.

Compounds of formulae (IV), (V) (VI) and (VIII) are known compounds or can be made from known compounds by conventional methods.

Compounds of formula (II) wherein $R^4$ is haloalkyl can be prepared by reacting a compound of formula (II) wherein $R^4$ is bromo or iodo with an appropriate haloalkyl iodide at elevated temperatures in the presence of copper powder as described for example by Kobayashi et al (Chem.Pharm.Bull (Japan) 1970, 18, 2334–2339) and by the method described by Carr et al ( J.Chem.-Soc. Perkin Trans. I. 1988 p 921–926).

Compounds of formula (I) where $R^7$ is a COOH group may be produced by hydrolysis of an appropriate ester; derivatives of the acid e.q. esters, amides, aldehydes may be produced by conventional procedures.

Compounds of formula (I) where $R^5$ or $R^6$ is chlorine or bromine and $R^7$ is $CO_2R^8$ may be produced by halogenation of the corresponding compound where $R^5$ and $R^6$=H. Suitable reagents include NBS or chlorine gas in the presence of light or radical inhibitors. The halo ester obtained can be converted to other acid derivatives by standard means.

The compounds of the invention are capable of controlling the growth of a wide variety of plants and in particular some show a useful selectivity in crops such as rice, cereals, maize, soya and sugar beet while others show broad spectrum activity. They may be applied to the soil before the emergence of plants (pre-emergence application) or they may be applied to the above ground parts of growing plants (postemergence application). In general the compounds are more active by post emergence application. In another aspect, therefore, the invention provides a process of inhibiting the growth of unwanted plants, by applying to the plants, or to the locus thereof, a compound of the formula (I) as hereinbefore defined. The rate of application required to inhibit the growth of unwanted plants will depend on, for example, the particular compound of formula (I) chosen for use, and the particular species of plant it is desired to control. However, as a general guide, an amount of from 0.01 to 5.0 kilograms per hectare, and preferably 0.025 to 2 kilograms per hectare is usually suitable.

The compounds of the invention are preferably applied in the form of a composition, in which the active ingredient is mixed with a carrier comprising a solid or liquid diluent In another aspect, therefore, the invention provides a herbicidal composition, comprising as an active ingredient a compound of the formula (I) as hereinbefore defined, in admixture with a solid or liquid diluent. Preferably the composition also comprises a surface active agent.

The solid compositions of the invention may be for example, in the form of dusting powders, or may take the form of granules. Suitable solid diluents include, for example, kaolin, bentonite, kieselquhr, dolomite, calcium carbonate, talc, powdered magnesia, and Fuller's earth. Solid compositions also include soluble powders and granules which may comprise a compound of the invention in admixture with a watersoluble carrier.

Solid compositions may also be in the form of dispersible powders or grains comprising in addition to the active ingredient, a wetting agent to facilitate the dispersion of the powder or grains in liquids. Such powders or grains may include fillers, suspending agents and the like.

Liquid compositions include solutions, dispersions and emulsions containing the active ingredient preferably in the presence of one or more surface active agents. Water or organic liquids may be used to prepare solutions, dispersions, or emulsions of the active ingredient. The liquid compositions of the invention may also contain one or more corrosion inhibitors for example lauryl isoquinolinium bromide.

Surface active agents may be of the cationic, anionic or non-ionic type. Suitable agents of the cationic type include for example quaternary ammonium compounds, for example cetyltrimethylammonium bromide. Suitable agents of the anionic type include for example soaps, salts of aliphatic mono-esters of sulphuric acid, for example sodium lauryl sulphate; and salts of sulphonated aromatic compounds, for example dodecylbenzenesulphonate, sodium, calcium and ammonium lignosulphonate, butylnaphthalene sulphonate, and a mixture of the sodium salts of diisopropyl- and triisopropylnaphthalenesulphonic acid. Suitable agents of the nonionic type include, for example, the condensation products of ethylene oxide with fatty alcohols such as oleyl alcohol and cetyl alcohol, or with alkyl phenols such as octylphenol, nonylphenol, and octylcresol. Other nonionic agents are the partial esters derived from long chain fatty acids and hexitol anhydrides, for example sorbitol monolaurate; the condensation products of the said partial esters with ethylene oxide and the lecithins; and silicone surface active agents (water soluble surface active agents having a skelton which comprises a siloxane chain e.q. Silwet L77). A suitable mixture in mineral oil is Atplus 411F.

The compositions which are to be used in the form of aqueous solutions, dispersions or emulsions are generally supplied in the form of a concentrate containing a high proportion of the active ingredient, the concentrate being diluted with water before use. These concentrates are usually required to withstand storage for prolonged periods and after such storage to be capable of dilution with water in order to form aqueous preparations which remain homogeneous for a sufficient time to enable them to be applied by conventional spray equipment.

The compositions of the invention may contain, in addition to carriers and surface active agents, various other constituents to increase their usefulness. They may contain, for example, buffering salts to maintain the pH of the composition within a desired range; antifreeze agents, for example urea or propylene glycol; adjuvants, for example oils and humectants; and sequestrates, for example citric acid and ethylenediaminetetracetic acid, which help to prevent the formation of insoluble precipitates when the compositions are diluted with hard water. Aqueous dispersions may contain anti-settling agents and anti-caking agents. The compositions may in general contain a dye or pigment to impart a characteristic colour. Agents for increasing viscosity may be added to reduce the formation of fine droplets during spraying, and thereby reduce spray drift. Other additives useful for particular purposes will be known to those skilled in the formulation art.

In general, concentrates may conveniently contain from 10 to 85% and preferably from 25 to 60% by weight of active ingredient. Dilute preparations ready for use may contain varying amounts of the active ingredient, depending upon the purpose for which they are to be used; however, dilute preparations suitable for many uses contain between 0.01% and 10% and preferably between 0.1% and 1% by weight of the active ingredient.

The compounds of the invention can be used in association with another herbicide, for example in the form of a mixture or in a composition of the invention.

The other herbicide will generally be a herbicide having a complementary action, depending upon the particular utility and circumstances of administration.

Examples of useful complementary herbicides are: For example it may be desirable in certain circumstances to use the compound of formula (II) or(IIA) in admixture with a contact herbicide.

Examples of useful complementary herbicides include:

A. benzo-2,1,3-thiadiazin-4-one-2,2-dioxides such as 3-isopropylbenzo-2,1,3-thiadiazin-4-one-2, 2-dioxide (bentazon);

B. hormone herbicides, particularly the phenoxy alkanoic acids such as 4-chloro-2-methylphenoxy acetic acid (MCPA), S-ethyl 4-chloro-O-tolyloxy thio-acetate (MCPA-thioethyl), 2-(2,4-dichlorophenoxy) propionic acid (dichlorprop), 2,4,5-trichlorophenoxyacetic acid (2,4,5-T), 4-(4-chloro-2-methylphenoxy)-butyric acid (MCPB), 2,4-dichlorophenoxyacetic acid (2,4-D), 4-(2,4-dichlorophenoxy)butyric acid (2,4-DB), 2-(4-chloro-2-methylphenoxy) propionic acid (mecoprop), 3,5,6-trichloro-2-pyridyloxyacetic acid (trichlopyr), 4-amino-3,5-dichloro-6-fluoro- 2-pyridyloxyacetic acid (fluroxypyr), 3,6-dichloropyridine-2-carboxylic acid (clopyralid), and their derivatives (eq. salts, esters and amides);

C. 1,3 dimethylpyrazole derivatives such as 2-[4-(2,4-dichlorobenzoyl) 1,3-dimethylpyrazol-5-yloxy]acetophenone (pyrazoxyfen), 4-(2,4-dichlorobenzoyl)1,3-dimethylpyrazol-5-yltoluene suphonate (pyrazolate) and 2-[4-(2,4-dichloro-m-toluolyl)-1,3-dimethylpyrazol-5-yloxy]-4′-methylacetophenone (benzofenap);

D. Dinitrophenols and their derivatives (e.g. acetates such as 2-methyl-4,6-dinitrophenol (DNOC), 2-t-butyl-4,6-dinitrophenol (dinoterb), 2-secbutyl-4,6-dinitrophenol (dinoseb) and its ester, dinoseb acetate;

E. dinitroaniline herbicides such as N′,N′-diethyl2,6-dinitro-4-trifluoromethyl-m-phenylenediamine (dinitramine), 2,6-dinitro-N,N-dipropyl4-trifluoromethylaniline (trifluralin), N-ethyl-N-(2-methylallyl)-2,6-dinitro-4-trifluoromethylaniline (ethalflurolin), N-(1-ethylpropyl)-2,6-dinitro-3,4-xylidine (pendimethalin); and 3,5-dinitro-$N^4$, $N^4$-dipropylsulphanilamide (oryzalin);

F. arylurea herbicides such as N′-(3,4-dichlorophenyl)-N,N-dimethylurea (diuron), N,N-dimethyl-N′-[3-(trifluoromethyl) phenyl]urea (flumeturon), 3-(3-chloro-4-methoxyphenyl)-1, 1-dimethylurea(metoxuron), 1-butyl-3-(3,4-dichlorophenyl)-1-methylurea(neburon), 3-(4-isopropylphenyl)- 1,1-dimethylurea (isoproturon), 3-(3-chloro-p-tolyl)-1,1-dimethylurea (chlorotoluron), 3-[4-(4- chlorophenoxy) phenyl]-1, 1-dimethylurea (chloroxuron), 3-(3,4-dichlorophenyl)-1-methylurea (linuron), 3-(4-chlorophenyl)-1-methoxy-1-methylurea (monolinuron), 3-(4-bromo-4-chlorophenyl)-1-methoxy-1-methylurea (chlorobromuron), 1-(1-methyl-1-phenylethyl)-3-p-tolylurea(daimuron), and 1-benzothiazol-2-yl-1,3-dimethylurea (methabenzthiazuron);

G. phenylcarbamoyloxyphenylcarbamates such as 3-[methoxycarbonylamino]phenyl (3-methylphenyl)-carbamate (phenmedipham) and 3-[ethoxycarbonylamino]-phenyl phenylcarbamate (desmedipham);

H. 2-phenylpyridazin-3-ones such as 5-amino-4-chloro-2-phenylpyridazin-3-one (pyrazon), and 4-chloro-5-methylamino-2-α,α,α-trifluoro-m-tolyl) pyridazin-3(2H)-one (norflurazon);

I. uracil herbicides such as 3-cyclohexyl-5,6-trimethyleneuracil (lenacil), 5-bromo-3-secbutyl-6-methyluracil (bromacil) and 3-t-butyl-5-chloro-6-methyluracil (terbacil);

J. triazine herbicides such as 2-chloro-4-ethylamino-6-(i-propylamino)-1,3,5-triazine (atrazine), 2-chloro-4,6-di(ethylamino)-1,3,5-triazine (simazine), 2-azido-4-(i-propylamino)6-methylthio-1,3,5-triazine (aziprotryne), 2-(4-chloro-6-ethylamino-1,3,5-triazin-2-ylamino)-2-methylpropionitrile (cyanazine), $N^2$, $N^4$-di-isopropyl-6-methylthio-1,3,5-triazine-2,4-diamine (prometryne), $N^2$-(1,2-dimethylpropyl) -$N^4$-ethyl-6-methylthio-1,3,5-triazine-2,4 -diamine (dimethametryne), $N^2$,$N^4$-diethyl-6-methylthio-1,3,5-triazine-2,4-diamine (simetryne), and $N^2$-tert-butyl-$N^4$-ethyl-6-methylthio-1,3,5-triazine-2,4-diamine (terbutryne);

K. phosphorothioate herbicides such as S-2-methylpiperidinocarbonyl-methyl O,O-dipropyl phosphorodithioate (piperophos), S-2-benzenesulphonamidoethyl O,O-di isopropyl phosphonodithioate (bensulide), and O-ethyl O-6-nitro-m-tolyl sec-butylphosphoamidothioate (butamifos);

L. thiolcarbamate herbicides such a S-ethyl N-cyclohexyl-N-ethyl(thiocarbamate) (cycloate), S-propyl dipropyl-thiocarbamate (vernolate), S-ethylazepine-1-carbothioate (molinate), S-4-chlorobenzyl diethylthiocarbamate (thiobencarb), S-ethyl di-isobutyl-thiocarbamate (butylate)*, S-ethyl diisopropylthiocarbamate (EPTC)*, S-2,3,3-trichloroallyl di-isopropyl (thiocarbamate) (tri-allate), S-2, 3-dichloroallyl di-isopropyl (thio-carbamate) (diallate), S-benzyl 1,2-dimethylpropyl (ethyl) thiocarbamate (esprocarb), S-benzyl di(secbutyl)thiocarbamate (triocarbazil), 6-chloro-3-phenylpyridazin 4-yl S-octyl thiocarbamate (pyridate), and S-1-methyl-1phenylethylpiperidine -1-carbothioate (dimepiperate);

M. 1,2,4-triazin-5-one herbicides such as 4-amino- 4,5-dihydro-3-methyl-6-phenyl-1,2,4-triazine-5-one(-metamitron) and 4-amino-6-t-butyl-4,5-dihydro-3-methylthio-1,3,4-triazin-5-one (metribuzin);

N. benzoic acid herbicides such as 2,3,6-trichlorobenzoic acid (2,3,6-TBA), 3,6-dichloro-2-methoxy-benzoic acid (dicamba) and 3-amino-2, 5-dichloro benzoic acid (chloramben);

O. anilide herbicides such as 2-chloro-2′,6′ -diethyl-N-(2-propoxyethyl)acetanilide (pretilachlor), N-butoxymethyl-chloro-2′, 6′-diethylacetanilide (butachlor), the corresponding N-methoxy compound (alachlor), the corresponding N-i-propyl compound (propachlor), 3′,4′-dichloropropionilide (propanil), 2-chloro-N-[pyrazol-1-ylmethyl]acet-2′-6′ xylidide (metazachlor),2-chloro-6′-ethyl-N-(2-methoxy-1-methylethyl)acet-O-toluidide (metolachlor), 2-chloro-N-ethoxymethyl-6′-ethylacet-O-toluidide (acetochlor), and 2-chloro-N-(2-methoxyethyl)acet-2′,6′-xylidide (dimethachlor);

P. dihalobenzonitrile herbicides such as 2,6-dichlorobenzonitrile (dichlobenil), 3,5-dibromo-4-hydroxybenzonitrile (bromoxynil) and 3,5-diiodo-4-hydroxybenzonitrile (ioxynil);

Q. haloalkanoic herbicides such as 2,2-dichloropropionic acid (dalapon), trichloroacetic acid (TCA) and salts thereof;

R. diphenylether herbicides such as ethyl 2-[5-( 2-chloro-trifluoro-p-tolyloxy)-2-nitrobenzoyloxy propionate (lactofen), D-[5-(2-chloro-, , -trifluoro-p-tolyloxy)-2-nitrobenzoyl] glycolic acid (fluroglycofen) or salts or ester thereof, 2,4-dichlorophenyl-4-nitrophenyl ether (nitrofen), methyl-(2,4-dichlorophenoxy)-2-nitrobenzoate (bifenox), 2-nitro-5-(2-chloro-4-trifluoromethyl-phenoxy) benzoic acid (acifluorfen) and salts and esters thereof, 2-chloro-4-trifluoromethylphenyl 3-ethoxy- 4-nitrophenyl ether (oxyfluorfen) and 5-(2- chloro-4-(trifluoromethyl)-phenoxy)-N-(methylsulfonyl)-2-nitrobenzamide (fomesafen); 2,4,6-trichlorophenyl 4-nitrophenyl ether (chlornitrofen) and 5-(2,4-dichlorophenoxy)-2-nitroanisole (chlomethoxyfen);

S. phenoxyphenoxypropionate herbicides such as (RS)-2-[4-(2,4-dichloro-phenoxy)phenoxy) propionic acid (diclofop) and esters thereof such as the methyl ester, 2-(4-(5-trifluoromethyl)-2-(pyridinyl)oxy) phenoxypropanoic acid (fluazifop) and esters thereof, 2-(4-(3-chloro-5-trifluoro-methyl)-2-pyridinyl)oxy)phenoxy)propanoic acid (haloxyfop) and esters thereof, 2-(4-((6-chloro-2-quinoxalinyl)oxy)phenoxypropanoic acid (quizalofop) and esters thereof and (±)-2-[4-(6-chlorooenzoxazol-2-yloxy)phenoxy]propionic acid (fenoxaprop) and esters thereof such as the ethyl ester;

T. cyclohexanedione herbicides such as 2,2-dimethyl -4,6-dioxo-5-(1-((2-propenyloxy)imino)butyl) cyclohexane carboxylic acid (alloxydim) and salts thereof, 2-(1-ethoxyimino) butyl-5-(2-(ethylthio)-propyl)-3-hydroxy-2-cyclohexan-1-one(sethoxydim), 2-(1-ethoxyimino) butyl)-3-hydroxy-5-thian-3-ylcyclohex-2-enone (cycloxydim), 2-[1-(ethoxyimino)propyl]-3-hydroxy -5-mesitylcyclohex-2-enone(tralkoxydim), and (±) -2- (E)-1-[(E)-3-chloroallyloximino]propyl -5-[2-(ethylthio)propyl]-3-hydroxy-cyclohex-2-enone (clethodim);

U. sulfonyl urea herbicides such as 2-chloro-N (4-methoxy-6-methyl-1,3,5-triazin-2-yl)aminocarbonyl) benzenesulphonamide (chlorosulfuron), methyl 2-((((4,6-dimethyl-2-pyrimidinyl)amino)carbonyl-)amino)sulphonylbenzoic acid (sulfometuron), 2-(((3-(4-methoxy-6-methyl-1,3,5-triazin-2-yl)carbonyl) amino)-sulphonyl)benzoic acid (metsulfuron) and esters thereof; -(4,6-dimethoxypryrimidin-2-ylcarbamoylsuphamoyl)-O-toluic acid (benzsulfuron) and esters thereof such as the methyl 3-[3-(4-methoxy-6-methyl-1,3,5-triazin-2-yl)ureidosulphonyl]thiophene-2-carboxylate (DPX-M6313), 2-(4-chloro-6-methoxy pyrimidin-2-yl carbamoylsulphamoyl benzoic acid (chlorimuron) and esters such as the ethyl ester thereof 2-(4,6-dimethoxypyrimidin-2-ylcarbamoyl-sulphamoyl)-N, N-dimethylnicotinamide, 2-[4,6-bis(-difluoromethoxy) pyrimidin-2-ylcarbamoylsulphamoyl) benzoic acid (pirimisulfuron) and esters such as the methyl ester thereof, 2-[3-(4-methoxy-6-methyl-1,3,5-triazin-zyl)-3-methylureidosulphonyl) benzoic acid esters such as the methyl ester thereof (DPX-LS300) and 5-(4,6-dimethoxypyrimidin-2-ylcarbamoylsulphamoyl)-1-methylpyrazole-4-carboxylic acid (pyrazosulfuron);

V. imidazolidinone herbicides such as 2-(4,5-dihydro-4-isopropyl-4-methyl-5-oxoimidazol-2-yl) quinoline-3-carboxylic acid (imazaquin), methyl 6-(4-isopropyl-4-methyl-5-oxo-2-imidazolin-2-yl) -m-toluate and p-toluate isomer(imazamethabenz), 2-(4-isopropyl-4-methyl-5-oxo-2-imidazolin-2-yl) nicotinic acid (imazapyr) and isopropylammonium salts thereof, (RS)-5-ethyl-2-(4-isopropyl4-methyl-5-oxo-2-imidazolin-2-yl)nicotinic acid (imazethapyr);

W. arylanilide herbicides such as benzoyl-N-(3-chloro-4-fluorophenyl)-L-alanine (flamprop) and esters thereof, ethyl N-benzoyl-N-(3,4-dichlorophenyl)-DL-alaninate (benzoylpropethyl), N-(2,4-difluorophenyl)-2-(3-trifluoromethyl)phenoxy)-3-pyridinecarboxamide (diflufenican); and amino acid herbicides such as trimethylsulfonium N-(phosphonomethyl)-glycine (sulphosate), glyphosate and bialaphos;

Y. organoarsenical herbicides such as monosodium methanearsonate (MSMA);

Z. herbicidal amide derivative such as (RS)-N,N-diethyl-2-(1-naphthyloxypropionamide) (napropamide), 3,5-dichloro-N-(1,1dimethylpropynyl)benzamide (propyzamide), (R)-1-(ethylcarbamoyl)ethyl carbanilate (carbetamide), N-benzyl-N- isopropylpivalamide (tebutam), (RS)-2-bromo- N-(α,α-dimethylbutyzamide (bromobutide), N-[3-(1-ethyl-1-methylpropyl)-isoxazol-5-yl]2,6-dimethoxybenzamide, (isoxaben), N-phenyl-2-(2-naphthyloxy) propionamide (naproanilide), N,N -dimethyl-diphenylacetamide (diphenamid), and N-(1-naphthyl)-phthalamic acid (naptalam);

AA. miscellaneous herbicides including 2-ethoxy-2,3-dihydro-3, 3-dimethylbenzofuran methanesulfonate (ethofumesate), 7-oxabicyclo (2.2.1)heptane,1-methyl-4-(1-methylethyl)-2-(2-methylphenylmethoxy)-exo (cinmethylin), 1,2-dimethyl-3,5-diphenylpyrazolium ion (difenzoquat) and sàlts thereof such as the methyl sulphate salt, 2-(2-chlorobenzyl)-4,4-dimethyl-1,2-oxazoldin -3-one (clomazone), 5-tert-butyl-3-(2,4-dichloro-5-isopropoxyphenyl)-1,3,4-oxadiazol-2(3H)-one (oxadiazon), 3,5-dibromo-4-hydroxy benzaldehyde 2,4-dinitrophenyloxime (bromofenoxim), 4-chlorobut-2-ynyl-3-chlorocarbanilate (barban), (RS)-2-(3,5-dichlorophenyl)-2-(2,2, 2-trichloroethyl-)oxirane (tridiphane), (3RS,4RS; 3RS,4SR)-3-chloro-4-chloromethyl-1-(α,α,α-trifluro-m-tolyl)-2-pyrrolidone (in the ratio 3:1) (fluorodichloridone), dichloroquinoline 8-carboxylic acid (quinchlorac) and 2-(1,3-benzothiazol-2-yl- oxy)-N-methylacetanilide (mefanacet);

BB. Examples of useful contact herbicides include:
bipyridylium herbicides such as those in which the active entity is the 1,1'-dimethyl-4,4'-bipyridylium ion (paraquat) and those in which the active entity is the 1,1'-ethylene-2,2'-bipyridylium ion (diquat);

These compounds are preferably employed in combination with a safener such as 2,2-dichloro -N,N-di-2-propenylacetamide (dichlormid)

The complementary herbicide is suitably present in the mixture or composition in an amount such that it is applied at its conventional rate.

The following Examples illustrate the invention.

EXAMPLE 1

This Example illustrates the preparation of compound Number 40 in Table II.

3-chloro-4,5-difluorobenzotrifluoride (1.08 g) was dissolved in dry dimethylsulphoxide (15 $cm^3$) and 4-chlororesorcinol (0.72 g) added portionwise followed by anhydrous potassium carbonate (1.38 g). The reaction mixture was stirred and heated to ca. 60° C. for 4 hours. It was then left to stand at room temperature for two days an subsequently poured into excess water and acidified with dilute hydrochloric acid.

After two extractions into ethyl acetate, the combined extract was washed with water and brine and dried over magnesium sulphate. Concentration gave compound 40 as a brown orange oil (0.42 g).

Compounds 37, 38, 41, 43, and 54 were prepared by analogous methods using appropriate reactants.

EXAMPLE 2

This Example illustrates the preparation of Compound No. 1 in Table I.

Compound Number 40 produced as described in Example 1, (5 g) was dissolved in dry dimethyl sulphoxide (50 $cm^3$) and potassium carbonate (2.1 g) added. Ethyl chlorofluoroacetate (2.1 g) in dimethyl sulphoxide (10 $cm^3$) was then added.

The mixture was stirred and heated at 90° C. for 5 hours, cooled and left to stand at room temperature overnight, poured into excess water and acidified with 2M hydrochloric acid. After extraction into diethyl ether the extract was washed with water, dried and concentrated to yield . Compound 1 as an oil (5.73 g).

Compounds 3, 11, 12, 13, 14, 16, 25, 26, 27, 28, 29, 30, 34 and 36 were prepared by analogous methods using appropriate reactants.

EXAMPLE 3

This Example illustrates the preparation of compound number 2 in Table I.

Step a 3-methoxyphenol (2.48 g) was dissolved in dimethylformamide (20 $cm^3$) and sodium hydride (0.48 g) added slowly. The reaction mixture was stirred at room temperature for half an hour. A solution of 3-chloro-4,5-difluorobenzotrifluoride (4.32 g) in dimethylformamide (10 $cm^3$) was then added dropwise. The reaction mixture was stirred at room temperature for 3 hours and subsequently poured into ice/water and acidified with dilute hydrochloric acid.

After extraction with diethyl ether the extract was washed, dried and concentrated to give compound of formula:

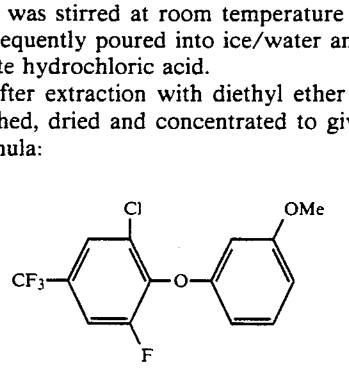

as an oil (5.49 g).

Step b

A sample of the oil produced as in step a (10.01 g) was dissolved in acetic anhydride (60 $cm^3$), stirred and a solution of copper II nitrate (7.54 g) in glacial acetic acid was added dropwise with stirring. After further stirring at room temperature for 5 hours, the reaction mixture was poured into excess water and extracted with diethyl ether. The extract was washed, dried and concentrated to give an oil which on trituration with pentane yielded a yellow solid (8.05 g) of formula:

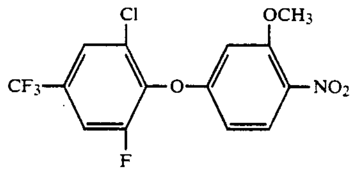

m.p. 100–103° C.

Step c

This procedure describes the preparation of compound 39 in Table II. The compound produced in step b (3.66 g) was dissolved in dry dichloromethane (20 $cm^3$), cooled in a solid carbon dioxide/IPA bath to −60° C. and placed under nitrogen atmosphere. A solution of boron tribomide (2.51 g) in dichloromethane was added slowly dropwise ensuring the temperature did not rise above −50° C. Once addition was complete the reaction mixture was allowed to attain room temperature and then poured into excess ice/water and extracted with dichloromethane. The extract was dried and concentrated to give a dark viscous oil which on distillation under high vacum yielded an orange oil which solidified on standing to yield compound 39 (2.91 g) as a yellow solid.

Step d

Compound number 39 (0.5 g), produced as described in step c was added to sodium hydride (0.04 g) suspended in DMF (1 $cm^3$). A solution of ethyl chlorofluoroacetate (0.2 g) in DMF (1 $cm^3$) was added dropwise.

The mixture was stirred and heated at 100° C. for 6 hours, poured into iced water, acidified with dilute hydrochloric acid and extracted with diethyl ether. After extraction the extract was washed, dried and concentrated to give an oil which was then separated using t.l.c. with an eluent of diethyl ether 60: hexane 40: acetic acid 5. The middle band was isolated and compound 2 obtained as a viscous oil (0.157 g).

Compounds 4, 15 and 17 were prepared by analogous methods using appropriate reactants.

EXAMPLE 4

This Example illustrates the preparation of compound number 5 in table I.

A sample of compound 1 (4.17 g) prepared as described in Example 2 was dissolved in isopropanol (60 $cm^3$) and a 1.1M solution of sodium hydroxide in water (10 $cm^3$) was added dropwise. The reaction mixture was refluxed at 100° C. for 4 hours. After cooling and being left to stand overnight the mixture was poured into excess water, and acidified with dilute hydrochloric acid. After two extractions into diethyl ether, the combined extract was washed, dried and concentrated to an oil. Trituration with pentane, filtering and drying yielded compound 5 (2.115 g) as an off white solid.

EXAMPLE 5

This Example illustrates the preparation of compound number 6 in Table I.

A sample of compound 5 prepared as described in Example 4 (0.63 g) was dissolved in analar methanol (15 $cm^3$) and a few drops of concentrated sulphuric acid were added. The reaction mixture was stirred and refluxed for 5 hours. It was then left to stand at room temperature overnight, concentrated on a rotavapour, diluted with water and extracted into diethyl ether. The extract was washed, dried and concentrated to give an oil which then separated using t.l.c. with a diluent of hexane 60: diethyl ether 30: acetic acid 5. Compound 6 was isolated as a viscous yellow oil (0.471 g).

Compound numbers 7, 18 and 19 were prepared by analogous methods using the appropriate reactants.

EXAMPLE 6

This Example illustrates the preparation of Compound Number 8 in Table I.

Compound Number 40 (0.51 g), produced as described in Example 1, was dissolved in dry DMF (10 $cm^3$) and sodium hydride (0.04 g) added, followed by a solution of ethyl bromodifluoroacetate (0.31 g) in DMF (2 $cm^3$). The reaction mixture was left to stand at room temperature overnight and then poured into water, acidified with 2M hydrochloric acid and extracted with diethyl ether. The extract was washed, dried and concentrated to give a viscous orange-brown oil which was separated using t.l.c. with an eluent of diethyl ether 30: hexane 60: acetic acid 5. The relevant band was isolated and compound 8 obtained as an oil (0.082 g).

EXAMPLE 7

This Example illustrates the preparation of Compound Number 9 in Table I.

A sample of compound 5 (0.5 g) prepared as described in Example 4 was dissolved in thionyl chloride (10 $cm^3$) and the mixture refluxed for 1½ hours. The mixture was then concentrated and azeotroped with toluene. The resulting oil was dissolved in dry toluene (15 $cm^3$) and dimethylamine bubbled through the solution for 5 minutes. The reaction was stirred for 2 hours and left at room temperature overnight. The mixture was concentrated, water added and extracted with ethyl acetate. The extract was washed, dried and concentrated to give an oil which was separated using t.l.c. with a diluent of diethyl ether 30: hexane 60: acetic acid 5. Compound 9 was isolated as an oil (0.385 g).

Compounds 20, 21 and 24 were produced by analagous methods using appropriate reactants.

EXAMPLE 8

This example illustrates the preparation of compound Number 42 in Table II. A sample of the oil (3.21 g) produced as described in step a of Example 3 was dissolved in dichloromethane (15 $cm^3$) and cooled to −70° C. A 1M solution of boron tribromide in dichloromethane (10 $cm^3$) was added dropwise. When addition was complete, the reaction mixture was allowed to attain room temperature and then stirred for 4 hours. After leaving overnight the reaction mixture was added to ice and the organic solution diluted with more dichloromethane. The organic solution was washed with water, dried over magnesium sulphate and concentrated to give a Compound number 42 as an oil (3.195 g).

EXAMPLE 9

This Example illustrating the preparation of compound number 10 in Table I.

A sample compound 42 produced as described in Example 8 (0.92 g) was dissolved in dry dimethyl sulphoxide (15 $cm^3$), anhydrous potassium carbonate (0.83 g) was added and the reaction mixture was stirred. A solution of ethyl chlorofluoroacetate (0.42 g) in dry dimethyl sulphoxide was added dropwise and the reaction mixture stirred and heated to 100° C. for three hours before being left to stand overnight. The reaction mixture was diluted with water and acidified with dilute hydrochloric acid. After extraction with diethyl ether the extract was washed, dried and concentrated to give compound 10 which was purified by preparative tlc using diethyl ether 30: hexane 60: acetic acid: 5 to give the product as viscous green-yellow oil (0.232 g).

EXAMPLE 10

This Example illustrates the preparation of compound number 46 in Table II.

Step a 2,4-dimethoxybenzonitrile (2 g) was mixed with pyridinium chloride (5.67 g) and the reaction mixture was fused at 210° C. for 2 hours. After being left to stand at room temperature overnight, the mixture was diluted with water and extracted into diethyl ether. The ether extracts were washed with water, dried over magnesium sulphate and concentrated to give a pink solid which was washed with petrol and air dried to give 2,4-dihydroxybenzonitrile (1.17 g) (m pt 176°–178° C.).

Step b

The product from step a was dissolved in dry dimethylsulphoxide (15 $cm^3$) and potassium carbonate (3.59 g) added. The mixture was stirred for ½ hour and then a solution of 3-chloro-4,5-difluorobenzotrifluoride (1.88 g) in dimethylsulphoxide (5 $cm^3$) was added. The reaction mixture was heated to ca 100° C. and stirred for 3 hours. After being left to stand overnight the reaction mixture was poured into an excess of water, acidified with 2m hydrochloric acid solution, and extracted into diethyl ether. The ether extracts were washed, dried and concentrated to give an oil. Separation using preparative T.L.C. using diethyl ether/hexane/acetic acid in the ratio 30:60:5 yielded the Compound Number 46 (m.pt 142°-144° C.).

EXAMPLE 11

This Example illustrates the preparation of compound number 23 in Table I.

Compound 46 produced as described in Example 10 (0.663 g) was dissolved in dry dimethyl sulphoxide (10 $cm^3$) and anhydrous potassium carbonate (0.41 g) added. The mixture was stirred for ½ hour, and a solution of ethyl chlorofluoroacetate (0.281 g) in dimethylsulphoxide (3 $cm^3$) added. A catalytic amount of potassium iodide was added and the reaction mixture stirred and heated for 4 hours at ca 80° C. The mixture was left for 48 hours and then poured into excess water and acidified with 2M hydrochloric acid solution. It was extracted into diethyl ether and the extracts washed dried and concentrated to give an oil. Separation by preparative TLC using an eluent diethyl ether/hexane/acetic acid in the ratio 30:60:5. yielded compound 23 (0.437 g) as an oil. The structure was confirmed by n.m.r. and i.r. spectroscopy.

EXAMPLE 12

This Example illustrates the preparation of compound number 22 in Table I.

A sample of co-pound 5 prepared as described in Example 4 (0.63 g) was dissolved in dry dichloromethane (10 $cm^3$) and tert butanol (0.22 g) was added followed by 4-dimethylaminopyridine (0.04 g). The mixture was cooled to 0° C. and N,N-dicyclohexylcarbodiimide (0.31 g) in dichloromethane (5 $cm^3$) was added. The reaction mixture was stirred for 30 minutes, allowed to attain room temperature and stirred for a further 4 hours. After standing overnight, the reaction mixture was filtered and the filtrate concentrated to an oily residue. The residue was separated using t.l.c. with a diluent of hexane 60: diethyl ether 30: acetic acid 5. The top band was isolated and compound 22 obtained as an oil (0.244 g).

EXAMPLE 13

This Example illustrates the preparation of compound 47 in Table II.

Sodium hydride (0.24 g of 55%) was washed with petrol then stirred in DMF (10 $cm^3$). The suspension was cooled in an ice/water bath. A solution of 2-methylresorcinol (0.6 g) and 3-chloro-4,5-difluorobenzotrifluoride (0.8 g) in DMF (10 $cm^3$) was added dropwise under nitrogen over a 30 minute period. The reaction mixture was then poured over a mixture of ice and 2M hydrochloric acid. The mixture was rapidly extracted with ether, washed and dried. After filtration and concentration, a pale yellow oil was obtained. The oil was separated using t.l.c. with an eluent of ether 60: hexane 40: acetic acid 5. The band at RF 6.5 was removed, and extracted to give compound 47 as a pale yellow oil (0.2 g).

Compounds 48, 49, 50, 51, 52 and 53 were prepared by analagous methods using appropriate reactants.

EXAMPLE 14

This Example illustrates the preparation of compound number 31 in Table I.

Step a

Compound Number 40 produced as described in Example 1 (3.4 g) was dissolved in dry DMSO (30 $cm^3$) and methyl bromoacetate (1.6 g) was added followed by potassium carbonate (3.5 g). The mixture was warmed to 75° C. and stirred for 4 hours. After cooling to room temperature the reaction mixture was poured onto ice and dilute hydrochloric acid. The resulting mixture was extracted with diethyl ether. The extract was washed, dried, filtered and concentrated to give

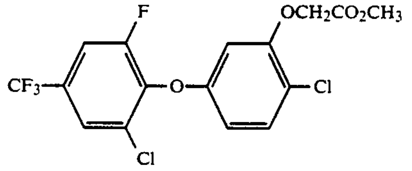

as an orange oil (3.5 g).

n.m.r. 7.6 (s, 1H); 7.4 (d, 1H); 7.3 (d, 1H); 6.55 (s, 1H); 6.35 (d, 1H); 4.7 (s, 2H); 3.8 (s, 3H).

Step b

The product from step (a) (1 g) was dissolved in carbon tetrachloride. N-bromo-succinimide (0.8 g) was added and the mixture stirred and refluxed, for 6 hours. The mixture filtered to remove a pale yellow solid. The filtrate was evaporated to give compound 31 as a yellow oil (0.35 g).

Compound 32 and 33 were prepared by analagous methods using appropriate reactants.

Biological Data

This data illustrates the herbicidal properties of compounds of Tables I and II. The compounds were submitted to herbicide tests as described below.

Each compound in the appropriate concentration was incorporated into a 4% emulsion of methyl cyclohexanone and a 0.4% blend of 3.6 parts Tween 20 and 1 part Span 80. Tween 20 is Trade Mark for a surface active agent comprising a condensate of 20 molar proportions of ethylene oxide with sorbitan laurate. Span 80 is a Trade Mark for a surface-active agent comprising sorbitan monolaurate. Formulation was effected by dissolving the compound in the requisite amount of solvent/surfactant blend, and diluting with water to a final spray volume of 45 ml. If the compound did not dissolve, glass beads were added, the total liquid volume adjusted to 5 ml with water and the mixture shaken to effect dispersion of the compound. The formulation so prepared, after removal of beads was then diluted to final spray volume (45 ml) with water.

The spray compositions so prepared were sprayed on to young pot plants (post-emergence test) at a rate equivalent to 1000 litres per hectare. Damage to plants was assessed 13 days after spraying by comparison with untreated plants, on a scale of 0 to 5 where 0 is 0-10% damage, 1 is 11 to 25% damage, 2 is 26-50% damage, 3 is 51-80% damage, 4 is 81-95% damage and 5 is 96-100% damage.

In a test carried out to detect pre-emergence herbicidal activity, seeds of the test species were placed on the surface of plastic trays of compost and sprayed with the compositions at the rate of 1000 litres per hectare. The seeds were then covered with further compost. 20 days after spraying, the seedlings in the sprayed plastic trays were compared with the seedlings in unsprayed control trays, the damage being assessed on the same scale of 0 to 5.

The results of the tests are given in Table III below.

TABLE III

| COMPOUND NO | RATE OF APPLICATION kg/ha | PRE- OR POST-EMERGENCE APPLICATION | TEST PLANTS (see Table IV) | | | | | | | | | | | | | | | | | | | | | | | | |
|---|---|---|---|---|---|---|---|---|---|---|---|---|---|---|---|---|---|---|---|---|---|---|---|---|---|---|---|
| | | | Sb | Rp | Ct | Sy | Mz | Ww | Rc | Bd | Ip | Am | Pi | Ca | Ga | Xa | Xs | Ab | Co | Av | Dg | Al | St | Ec | Sh | Ag | Cn |
| 1 | 1 | Pre | 3 | 5 | 1 | 3 | 0 | 0 | 0 | 4 | 4 | — | 4 | 5 | — | 3 | — | 5 | 2 | 0 | 2 | 0 | 3 | 1 | 0 | 5 | 1 |
| | 1 | Post | 4 | 5 | 4 | 5 | 4 | 3 | 3 | 5 | 5 | 5 | 5 | 5 | 5 | — | 5 | 5 | 5 | 3 | 4 | 3 | 5 | 5 | 5 | 3 | 3 |
| 2 | 1.25 | Pre | 5 | 5 | 2 | 1 | 3 | 3 | 1 | 5 | 4 | 5 | 5 | 5 | 4 | 5 | — | 5 | 4 | 3 | 4 | 3 | 5 | 4 | 4 | — | 1 |
| | 0.25 | Post | 3 | 5 | 4 | 2 | 4 | 3 | 2 | 5 | 5 | 5 | 4 | 4 | 5 | — | 5 | 5 | 4 | 4 | 4 | 3 | 4 | 3 | 4 | 2 | 3 |
| 3 | 1.25 | Pre | 5 | 5 | 3 | 2 | 0 | 0 | 0 | 5 | 4 | 5 | 5 | 5 | 4 | 0 | — | 5 | 2 | 0 | 0 | 0 | 2 | 0 | 0 | — | 0 |
| | 0.25 | Post | 3 | 5 | 4 | 4 | 4 | 1 | 2 | 5 | 5 | 5 | 3 | 5 | 5 | — | 5 | 5 | 3 | 2 | 1 | 1 | 2 | 4 | 4 | 0 | 2 |
| 4 | 1.25 | Pre | 5 | 5 | 1 | 4 | 0 | 0 | 0 | 4 | 4 | 5 | 3 | 5 | 4 | 3 | — | 5 | 4 | 0 | 0 | 0 | 3 | 0 | 1 | — | 0 |
| | 0.25 | Post | 3 | 5 | 5 | 4 | 3 | 3 | 3 | 5 | 5 | 5 | 4 | 5 | 5 | — | 5 | 5 | 4 | 3 | 3 | 3 | 3 | 0 | 4 | 2 | 3 |
| 5 | 1.25 | Pre | 5 | 5 | 1 | 3 | 0 | 1 | 0 | 5 | 4 | 5 | 2 | 5 | 3 | 2 | — | 3 | 2 | 0 | 0 | 0 | 0 | 0 | 0 | — | 0 |
| | 0.25 | Post | 2 | 5 | 4 | 3 | 1 | 0 | 3 | 2 | 5 | 5 | 2 | 5 | 3 | — | 4 | 1 | 2 | 1 | 2 | 2 | 2 | 3 | 3 | 1 | 0 |
| 6 | 1 | Pre | 4 | 5 | 2 | 4 | 0 | 0 | 0 | 5 | 5 | 5 | 4 | 5 | 5 | 4 | — | 5 | 1 | 0 | 0 | 0 | 0 | 0 | 0 | — | 0 |
| | 0.25 | Post | — | 5 | 5 | 4 | 4 | 2 | 1 | 5 | 5 | 5 | 3 | 5 | 5 | — | 5 | 5 | 3 | 2 | 4 | 2 | 4 | 3 | 4 | 2 | 2 |
| 7 | 1 | Pre | 4 | 4 | 3 | 2 | 0 | 1 | 0 | 5 | 5 | 5 | 4 | 5 | 4 | 2 | — | 4 | 3 | 0 | 0 | 0 | 0 | 0 | 0 | — | 0 |
| | 0.25 | Post | — | 5 | 5 | 3 | 1 | 2 | 2 | 5 | 5 | 5 | 5 | 5 | 5 | — | 5 | 5 | 2 | 2 | 5 | 2 | 4 | 4 | 5 | 3 | 1 |
| 8 | 0.6 | Pre | 3 | 1 | 1 | 0 | 0 | 0 | 0 | 4 | 2 | 4 | 2 | 4 | 4 | 0 | — | 2 | 1 | 0 | 0 | 0 | 0 | 0 | 0 | — | 0 |
| | 0.25 | Post | 3 | 5 | 4 | 3 | 0 | 2 | 1 | 3 | 5 | 5 | 3 | 5 | 5 | — | 5 | 5 | 2 | 0 | 3 | 1 | 3 | 3 | 3 | 0 | 1 |
| 9 | 1 | Pre | 3 | 1 | 0 | 3 | 0 | 2 | 0 | 0 | 4 | 5 | 4 | 5 | 4 | 0 | — | 4 | 0 | 1 | 0 | 3 | 1 | 2 | 0 | — | 0 |
| | | Post | 4 | 5 | 4 | 2 | 1 | 1 | 1 | 3 | 5 | 5 | 4 | 5 | 5 | — | 3 | 4 | 2 | 1 | 5 | 0 | 2 | 2 | 2 | 2 | 2 |
| 10 | 1 | Pre | 3 | 0 | 0 | 0 | 0 | 0 | 0 | 0 | 1 | 0 | 0 | 1 | 1 | 0 | — | 1 | 0 | 0 | 0 | 0 | 0 | 0 | 0 | — | 0 |
| | 1 | Post | 3 | 5 | 4 | 2 | 3 | 0 | 1 | 3 | 4 | 5 | 5 | 5 | 4 | — | 3 | 4 | 1 | 2 | 3 | 1 | 1 | 2 | 3 | 1 | 0 |
| 11 | 1 | Pre | 1 | 1 | 0 | 0 | 0 | 0 | 0 | 1 | 2 | 4 | 0 | 0 | 0 | 0 | — | 0 | 1 | 0 | 0 | 0 | 0 | 0 | 0 | — | 0 |
| | 0.25 | Post | — | 1 | 2 | 1 | 0 | 0 | 0 | 2 | 5 | 4 | 2 | 3 | 3 | — | 2 | 2 | 1 | 0 | 1 | 0 | 0 | 1 | 2 | 0 | 0 |
| 12 | 1 | Pre | 0 | 1 | 0 | 0 | 0 | 0 | 0 | 3 | 3 | 3 | 1 | 3 | 3 | 0 | — | 2 | 0 | 0 | 0 | 0 | 0 | 0 | 0 | — | 0 |
| | 0.25 | Post | — | 3 | 4 | 2 | 0 | 0 | 2 | 4 | 4 | 5 | 4 | 5 | 5 | — | 4 | 3 | 2 | 2 | 2 | 0 | 1 | 3 | 3 | 0 | 0 |
| 13 | 2 | Pre | 2 | 1 | 0 | 0 | 0 | 0 | 0 | 0 | 1 | 5 | 0 | 3 | 0 | 2 | — | 0 | 3 | 0 | 0 | 0 | 2 | 0 | 1 | — | — |
| | | Post | 3 | 3 | 2 | 4 | 2 | 0 | 0 | 2 | 5 | 5 | 3 | 3 | 5 | — | 3 | 5 | 2 | 0 | 2 | 0 | 3 | 2 | 2 | 0 | 2 |
| 14 | 1 | Pre | 3 | — | 1 | 1 | 0 | 0 | 0 | 3 | 4 | 5 | 3 | 5 | 4 | 0 | — | 4 | 2 | 0 | 1 | 0 | 3 | 0 | 0 | — | 0 |
| | 0.25 | Post | 0 | 5 | 5 | 4 | 4 | 1 | 1 | 5 | 5 | 5 | 4 | 5 | 5 | — | 5 | 5 | 0 | 0 | 5 | 2 | 3 | 2 | 5 | 1 | 3 |
| 15 | 1 | Pre | 3 | — | 3 | 3 | 1 | 0 | 0 | 5 | 5 | 5 | 5 | 5 | 4 | 3 | — | 3 | 5 | 1 | 3 | 0 | 4 | 1 | 4 | — | 0 |
| | 0.25 | Post | 0 | 5 | 5 | 4 | 4 | 1 | 0 | 5 | 5 | 5 | 5 | 5 | 5 | — | 5 | 5 | 3 | 1 | 5 | 1 | 3 | 3 | 5 | 0 | 1 |
| 16 | 1 | Pre | 2 | — | 1 | 0 | 0 | 0 | 0 | 2 | 2 | 5 | 3 | 5 | 2 | 1 | — | 4 | 0 | 0 | 0 | 0 | 0 | 0 | 4 | — | 0 |
| | 0.25 | Post | 0 | 5 | 5 | 5 | 2 | 2 | 1 | 5 | 5 | 5 | 4 | 5 | 5 | — | 5 | 5 | 2 | 1 | 5 | 1 | 4 | 3 | 3 | 0 | 0 |
| 17 | 1 | Pre | 3 | — | 3 | 0 | 1 | 1 | 0 | 5 | 4 | 5 | 3 | 2 | 3 | 4 | — | 5 | 3 | 4 | 3 | 1 | 4 | 4 | 1 | — | 0 |
| | 0.25 | Post | 0 | 5 | 5 | 4 | 3 | 1 | 0 | 5 | 5 | 5 | 5 | 5 | 5 | — | 5 | 5 | 0 | 1 | 5 | 1 | 5 | 3 | 5 | 0 | 0 |
| 18 | 1 | Pre | 4 | 5 | — | 3 | 1 | 2 | 2 | 5 | 5 | 5 | 3 | 5 | 4 | 4 | — | 5 | 4 | 0 | 2 | 0 | 3 | 3 | 1 | — | 3 |
| | 0.25 | Post | 5 | 5 | 5 | 5 | 5 | 2 | 2 | 5 | 5 | 5 | 5 | 5 | 5 | — | 5 | 5 | 5 | 2 | 4 | 1 | 5 | 4 | 4 | 1 | 2 |
| 19 | 1 | Pre | 5 | 5 | 0 | 3 | 2 | 0 | 0 | 4 | 4 | 5 | 1 | 4 | 3 | 1 | — | 4 | 2 | 0 | 4 | 0 | 3 | 0 | 0 | — | 0 |
| | 0.25 | Post | 5 | 5 | 5 | 5 | 4 | 3 | 2 | 5 | 5 | 5 | 5 | 5 | 5 | — | 5 | 5 | 5 | 2 | 5 | 2 | 5 | 4 | 4 | 2 | 1 |
| 20 | 1 | Pre | 4 | 4 | — | 3 | 1 | 0 | 2 | 5 | 4 | 5 | 1 | 4 | 3 | 4 | — | 4 | 2 | 0 | 0 | 0 | 2 | 1 | 0 | — | 0 |
| | 0.25 | Post | 5 | 5 | 5 | 5 | 4 | 3 | 2 | 5 | 5 | 5 | 4 | 5 | 5 | — | 5 | 5 | 5 | 2 | 4 | 1 | 4 | 3 | 4 | 1 | 1 |
| 21 | 1 | Pre | 5 | 5 | 0 | 3 | 1 | 1 | 3 | 5 | 5 | 5 | 5 | 5 | 4 | 2 | — | 5 | 4 | 0 | 0 | 0 | 2 | 2 | 2 | — | 0 |
| | 0.25 | Post | 5 | 5 | 5 | 4 | 4 | 2 | 3 | 5 | 5 | 5 | 4 | 5 | 5 | — | 5 | 5 | 4 | 1 | 5 | 1 | 5 | 3 | 5 | 2 | 1 |
| 22 | 1 | Pre | 4 | 5 | 0 | 3 | 1 | 1 | 1 | 4 | 5 | 5 | 3 | 5 | 3 | 2 | — | 4 | 2 | 2 | 4 | 0 | 5 | 4 | 3 | — | 3 |
| | 0.25 | Post | 5 | 5 | 5 | 5 | 5 | 2 | 1 | 5 | 5 | 5 | 4 | 5 | 5 | — | 5 | 5 | 5 | 1 | 5 | 1 | 4 | 4 | 4 | 2 | 2 |
| 23 | 1 | Pre | 4 | — | 2 | 5 | 3 | 1 | 0 | 5 | 5 | 5 | 5 | 5 | 5 | 4 | — | 5 | 4 | 1 | 4 | 0 | 4 | 4 | 3 | — | 0 |
| | 0.25 | Post | 0 | 5 | 5 | 5 | 3 | 2 | 1 | 5 | 5 | 5 | 5 | 5 | 5 | — | 5 | 5 | 5 | 1 | 5 | 2 | 5 | 5 | 5 | 1 | 3 |
| 24 | 1 | Pre | 5 | 5 | — | 4 | 0 | 1 | 2 | 4 | 5 | 4 | 0 | 5 | 4 | 3 | — | 3 | 4 | 0 | 0 | 0 | 3 | 1 | 0 | — | 0 |
| | 0.25 | Post | 5 | 5 | 5 | 5 | 4 | 3 | 2 | 5 | 5 | 5 | 4 | 5 | 5 | — | 5 | 5 | 4 | 1 | 4 | 1 | 4 | 4 | 5 | 1 | 1 |
| 25 | 1 | Pre | 5 | 5 | 1 | 0 | 0 | 0 | 1 | 4 | 4 | 5 | 5 | 5 | — | 2 | — | 5 | 3 | 0 | 0 | 0 | 0 | 0 | 2 | — | 0 |
| | 0.25 | Post | 5 | 5 | 4 | 4 | 4 | 1 | 1 | 5 | 5 | 5 | 3 | 5 | 5 | — | 4 | 5 | 3 | 1 | 4 | 1 | 4 | 3 | 4 | 1 | 0 |

TABLE III-continued

| COMPOUND NO | RATE OF APPLICATION kg/ha | PRE- OR POST-EMERGENCE APPLICATION | TEST PLANTS (see Table IV) Sb | Rp | Ct | Sy | Mz | Ww | Rc | Bd | Ip | Am | Pi | Ca | Ga | Xa | Xs | Ab | Co | Av | Dg | Al | St | Ec | Sh | Ag | Cn |
|---|---|---|---|---|---|---|---|---|---|---|---|---|---|---|---|---|---|---|---|---|---|---|---|---|---|---|---|
| 37 | 4 | Pre | 3 | 4 | 1 | 1 | 0 | 0 | 1 | 4 | 3 | 5 | 5 | 3 | — | 2 | — | 5 | 1 | 0 | 5 | 1 | 5 | 2 | 1 | 3 | 1 |
| | | Post | 3 | 3 | 4 | 4 | 2 | 3 | 2 | 4 | 5 | 5 | 5 | 4 | 5 | — | 3 | 5 | 3 | 3 | 4 | 3 | 3 | 4 | 4 | 1 | 2 |
| 38 | 4 | Pre | 4 | 5 | 2 | 1 | 2 | 2 | 1 | 3 | 4 | — | 5 | 4 | — | 3 | — | 4 | 3 | 1 | 5 | 2 | 5 | 0 | 0 | 3 | 1 |
| | | Post | 4 | 4 | 3 | 3 | 4 | 1 | 2 | 5 | 5 | 5 | 5 | 5 | 5 | — | 5 | 5 | 4 | 3 | 5 | 3 | 5 | 5 | 4 | 2 | 2 |
| 39 | 1.25 | Pre | 5 | 4 | 3 | 1 | 2 | 2 | 1 | 5 | 3 | 5 | 5 | 4 | 5 | 3 | — | 5 | 3 | 0 | 3 | 1 | 3 | 0 | 0 | — | 0 |
| | | Post | 2 | 5 | 4 | 3 | 4 | 3 | 3 | 3 | 5 | 5 | 5 | 5 | 5 | — | 4 | 5 | 3 | 3 | 4 | 3 | 4 | 3 | 3 | 3 | 3 |
| 40 | 1.25 | Pre | 2 | 4 | 1 | 0 | 0 | 0 | 1 | 3 | 1 | 4 | 5 | 1 | 3 | 0 | — | 4 | 0 | 0 | 2 | 0 | 0 | 0 | 0 | — | 0 |
| | | Post | 3 | 5 | 3 | 2 | 4 | 3 | 2 | 3 | 4 | 5 | 5 | 5 | 4 | — | 4 | 5 | 3 | 2 | 3 | 3 | 3 | 4 | 3 | 0 | 2 |
| 41 | 1.25 | Pre | 2 | 4 | 0 | 0 | 0 | 0 | 0 | 0 | 2 | 3 | 4 | 0 | 3 | 0 | — | 0 | — | 0 | 1 | 0 | 2 | 0 | 0 | — | 0 |
| | | Post | 2 | 4 | 4 | 2 | 2 | 2 | 2 | 3 | 3 | 5 | 4 | 5 | 4 | — | 4 | 4 | 3 | 2 | 3 | 2 | 3 | 4 | 3 | 2 | 2 |
| 43 | 4 | Pre | 1 | 0 | 2 | 1 | 0 | 0 | 0 | 0 | 0 | 4 | 1 | 3 | 0 | 0 | — | 2 | 1 | 0 | 0 | 0 | 1 | 0 | 2 | — | — |
| | | Post | 3 | 1 | 2 | 3 | 4 | 1 | 1 | 2 | 2 | 4 | 3 | 3 | 4 | — | 3 | 3 | 1 | 2 | 2 | 1 | 4 | 3 | 3 | 0 | 2 |
| 44 | 4 | Pre | 4 | 5 | 2 | 2 | 2 | 0 | 0 | 3 | 3 | 5 | 5 | 5 | 5 | 2 | — | 5 | 2 | 3 | 4 | 0 | 5 | 3 | 3 | — | — |
| | | Post | 5 | 4 | 5 | 5 | 5 | 2 | 2 | 5 | 5 | 5 | 5 | 5 | 5 | — | 5 | 5 | 2 | 3 | 5 | 3 | 5 | 5 | 5 | 3 | 3 |
| 46 | 1 | Pre | 2 | 0 | 0 | 0 | 0 | 0 | 0 | 0 | 0 | 3 | 2 | 2 | 3 | 1 | — | 2 | 3 | 0 | 2 | 0 | 2 | 0 | 2 | — | — |
| | 0.25 | Post | 1 | 0 | 0 | 3 | 4 | 0 | 1 | 1 | 3 | 5 | 3 | 0 | 3 | — | 0 | 0 | 0 | 1 | 2 | 0 | 3 | 2 | 2 | 0 | 2 |
| 47 | 1 | Pre | 1 | 1 | 0 | 0 | 0 | 0 | 0 | 0 | 2 | 4 | 4 | 1 | — | 0 | — | 3 | 0 | 0 | 0 | 0 | 1 | 0 | 3 | — | 0 |
| | 0.25 | Post | 2 | 3 | 4 | 4 | 4 | 1 | 0 | 2 | 5 | 5 | 3 | 3 | 4 | — | 2 | 4 | 0 | 1 | 3 | 1 | 2 | 2 | 2 | 0 | 1 |
| 55 | 1 | Pre | 0 | 0 | 2 | 0 | 0 | 0 | 0 | 1 | 0 | 2 | 0 | 3 | 0 | 0 | — | 0 | 2 | 0 | 0 | 0 | 0 | 0 | 0 | 0 | 0 |
| | 1 | Post | 1 | 0 | 1 | 2 | 3 | 0 | 0 | 0 | 2 | 0 | 0 | 2 | 0 | — | 0 | 1 | 0 | 0 | 2 | 0 | 2 | 1 | 2 | 0 | 0 |

TABLE IV

| Abbreviations used for Test Plants |
|---|
| Sb - Sugar Beet |
| Rp - Rape |
| Ct - Cotton |
| Sy - Soybean |
| Mz - Maize |
| Ww - Winter wheat |
| Rc - Rice |
| Bd - *Bidens pilosa* |
| Ip - *Ipomoea purpurea* |
| Am - *Amaranthus retroflexus* |
| Pi - *Polygonum aviculare* |
| Ca - *Chenopodium album* |
| Ga - *Galium aparine* |
| Xa - *Xanthium spinosum* |
| Ab - *Abutilon theophrasti* |
| Co - *Cassia obtusifolia* |
| Av - *Avena fatua* |
| Dg - *Digitaria sanguinalis* |
| Al - *Alopecurus myosuroides* |
| St - *Setaria viridis* |
| Ec - *Echinochloa crus-galli* |
| Sh - *Sorghum halepense* |
| Ag - *Agropyron repens* |
| Cn - *Cyperus rotundus* |

The herbicidal activity of some of the compounds was tested by an alternative method as follows:

Each compound in the appropriate concentration was incorporated into a 4% emulsion of methylcyclohexanone and 0.4% blend of 3.6 parts Tween 20 and 1 part Span 80. Tween 20 is a Trade Mark for a surface active agent comprising a condensate of 20 molar proportions of ethylene oxide with sorbitan laurate. Span 80 is a Trade Mark for a surface-active agent comprising sorbitan monolaurate. Formulation was effected by dissolving the compound in the requisite amount of solvent/surfactant blend, and diluting with water to a final spray volume of 45 ml. If the compound did not dissolve, glass beads were added, the total liquid volume adjusted to 5 ml with water and the mixture shaken to effect dispersion of the compound. The formulation so prepared, after removal of beads was then diluted to final spray volume (45 ml) with water.

The spray compositions so prepared were sprayed onto young pot plants (post-emergence test) at a rate equivalent to 1000 litres per hectare. Damage to plants was assessed 13 days after spraying by comparison with untreated plants, on a scale of 0 to 9 where 0 is 0% damage, 1 is 1-5% damage, 2 is 6-15% damage, 3 is 16-25% damage, 4 is 26-35% damage, 5 is 36-59% damage, 6 is 60-69% damage, 7 is 70-79% damage, 8 is 80-89% damage and 9 is 90-100% damage.

In a test carried out to detect pre-emergence herbicidal activity, crop seeds were sown at 2 cm depth (i.e. Sb, Ct, Rp, Ww, Rc, Sy) and weed seeds at 1 cm depth beneath compost and sprayed with the compositions at the rate of 1000 litres per hectare. 20 days after spraying, the seedlings in the sprayed plastic trays were compared with the seedlings in unsprayed control trays, the damage being assessed on the same scale of 0 to 9.

The results of the tests are given in Table V below.

TABLE V

| COMPOUND NO | RATE OF APPLICATION kg/ha | PRE- OR POST-EMERGENCE APPLICATION | TEST PLANTS (see Table VI) | | | | | | | | | | | | | | |
|---|---|---|---|---|---|---|---|---|---|---|---|---|---|---|---|---|---|
| | | | Sb | Rp | Ct | Sy | Mz | Rc | Ww | Pi | Ca | Ga | Am | Bd | Eh | Ip | Ab |
| 26 | 1 | Pre | 0 | 0 | 0 | 0 | 0 | 0 | 0 | 0 | 5 | — | 5 | 0 | 0 | 0 | 0 |
| | | Post | 2 | 9 | 9 | 9 | 7 | 1 | 3 | 9 | 9 | 9 | 9 | 9 | 9 | 9 | 9 |
| 27 | 1 | Pre | 0 | 0 | 0 | 0 | 0 | 0 | 0 | 0 | 0 | — | 0 | 0 | 0 | 0 | 0 |
| | 0.25 | Post | 4 | 9 | 3 | 6 | 3 | 0 | 2 | 5 | 1 | — | 9 | 3 | 2 | 4 | 7 |
| 28 | 1 | Pre | 0 | 3 | 7 | 5 | 0 | 0 | 0 | 0 | 0 | — | 0 | 5 | 0 | 0 | 0 |
| | | Post | 6 | 9 | 2 | 8 | 5 | 0 | 0 | 5 | 9 | 9 | 9 | 5 | 7 | 9 | 7 |
| 29 | 1 | Pre | 3 | 3 | 3 | 3 | 0 | 0 | 0 | 0 | 5 | — | 3 | 5 | 0 | 0 | — |
| | | | 3 | 2 | 2 | 0 | 4 | 0 | 0 | 2 | 3 | 0 | 2 | 0 | 0 | 5 | 3 |
| 30 | 1 | Pre | 6 | 5 | 5 | 4 | 0 | 4 | 3 | 9 | 9 | — | 9 | 3 | 9 | 0 | 4 |
| | | Post | 6 | — | 8 | 9 | 6 | 3 | 5 | 9 | 9 | 9 | 9 | 9 | 9 | 9 | 9 |
| 31 | 1 | Pre | 5 | 3 | 0 | 0 | 0 | 3 | 0 | 9 | 3 | — | 9 | 0 | 5 | 3 | — |
| | | Post | 9 | 9 | 5 | 6 | 6 | 4 | 5 | 9 | 9 | 8 | 9 | 8 | 9 | 7 | 8 |
| 32 | 1 | Pre | 4 | 4 | 0 | 0 | 3 | 0 | 5 | 9 | 8 | 2 | 9 | 0 | 8 | 0 | 5 |
| | | Post | 5 | 9 | 9 | 8 | 6 | 3 | 5 | 9 | 9 | 9 | 9 | 8 | 9 | 8 | 9 |
| 33 | 0.25 | Pre | 0 | 0 | 0 | 0 | 2 | 0 | 0 | 0 | 0 | 0 | 0 | 0 | 0 | 0 | 0 |
| | | Post | 9 | 9 | 9 | 9 | 5 | 2 | 5 | 9 | 9 | 9 | 9 | 9 | 9 | 9 | 9 |
| 34 | 1.5 | Pre | 0 | 6 | 0 | 0 | 0 | 0 | 0 | 0 | 9 | 5 | 9 | 0 | 0 | 0 | 0 |
| | | Post | 9 | 9 | 9 | 9 | 9 | 2 | 3 | 9 | 9 | 9 | 9 | 9 | 9 | 9 | 9 |
| 36 | 1 | Pre | 0 | 0 | 0 | 0 | 0 | 0 | 0 | 0 | 2 | — | 0 | 0 | 2 | 0 | 0 |
| | | Post | 9 | 7 | 9 | 9 | 8 | 1 | 7 | 8 | 9 | 9 | 9 | 5 | 9 | 9 | 9 |
| 50 | 1 | Pre | 4 | 0 | 0 | 0 | 0 | 0 | 0 | 0 | 0 | — | 0 | 0 | 0 | 0 | 0 |
| | | Post | 3 | 9 | 2 | 5 | 3 | 0 | 0 | 0 | 0 | — | 9 | 0 | 0 | 0 | 3 |
| 51 | 1 | Pre | 0 | 0 | 0 | 0 | 0 | 5 | 0 | 0 | 0 | — | 0 | 0 | 0 | 0 | 0 |
| | | Post | 1 | 5 | 0 | 0 | 0 | 2 | 0 | 5 | 6 | 1 | 9 | 0 | 2 | 0 | 1 |
| 52 | 1 | Pre | 0 | 0 | 0 | 0 | 0 | 0 | 0 | 0 | 0 | — | 0 | 0 | — | 0 | — |
| | | Post | 2 | 0 | 0 | 0 | 3 | 0 | 0 | 0 | 3 | 0 | 0 | 0 | 2 | 4 | 2 |
| 53 | 1 | Pre | 5 | 4 | 4 | 4 | 5 | 6 | 4 | 9 | 9 | — | 9 | 6 | 8 | 0 | 7 |
| | | Post | 5 | — | 6 | 8 | 5 | 3 | 4 | 9 | 9 | 9 | 9 | 5 | 6 | 8 | 8 |
| 54 | 0.25 | Pre | 0 | 0 | 0 | 0 | 1 | 9 | 0 | 0 | 0 | — | 0 | 0 | 3 | 9 | 0 |
| | | Post | 2 | 0 | 1 | 0 | 0 | 0 | 0 | 0 | 0 | 0 | 6 | 0 | 0 | 0 | 0 |

| COMPOUND NO | RATE OF APPLICATION kg/ha | PRE- OR POST-EMERGENCE APPLICATION | TEST PLANTS (see Table VI) | | | | | | | | | |
|---|---|---|---|---|---|---|---|---|---|---|---|---|
| | | | Xa | Xs | Av | Al | Ag | Sh | St | Dg | Ec | Ce |
| 26 | 1 | Pre | 0 | — | 0 | 0 | — | 0 | 0 | 0 | 0 | 0 |
| | | Post | — | 9 | 2 | 1 | 5 | 5 | 5 | 9 | 0 | 5 |
| 27 | 1 | Pre | 0 | — | 0 | 0 | — | 0 | 0 | 0 | 0 | 0 |
| | 0.25 | Post | — | 7 | 0 | 0 | 0 | 1 | 0 | 0 | 0 | 0 |
| 28 | 1 | Pre | 6 | — | 0 | 0 | — | 2 | 0 | 0 | 0 | 0 |
| | | Post | — | 3 | 0 | 0 | 0 | 1 | 1 | 2 | 1 | 0 |
| 29 | 1 | Pre | 0 | — | 5 | 0 | — | 0 | 6 | 5 | 0 | 0 |

TABLE V-continued

| | | | | | | | | | | | | |
|---|---|---|---|---|---|---|---|---|---|---|---|---|
| | | | — | 0 | 0 | 0 | 0 | 0 | 4 | 3 | 0 | 0 |
| 30 | 1 | Pre | 5 | — | 4 | 6 | — | 8 | 9 | — | 5 | 5 |
| | | Post | — | 9 | 5 | 3 | 5 | 8 | 5 | 7 | 7 | 0 |
| 31 | 1 | Pre | 0 | — | 5 | 3 | — | 0 | 6 | 0 | 3 | 0 |
| | | Post | — | 9 | 5 | 5 | 6 | 6 | 6 | 7 | 6 | — |
| 32 | 1 | Pre | 0 | — | 0 | 0 | — | 0 | 9 | 8 | 5 | 0 |
| | | Post | — | 8 | 5 | 5 | 3 | 6 | 5 | 8 | 6 | 4 |
| 33 | 0.25 | Pre | 0 | — | 0 | 0 | — | 0 | 4 | 4 | 0 | 0 |
| | | Post | — | 9 | 5 | 5 | 4 | 7 | 7 | 6 | 7 | 5 |
| 34 | 1.5 | Pre | 0 | — | 0 | 0 | — | 0 | 0 | 0 | 0 | 0 |
| | | Post | — | 9 | 2 | 2 | 2 | 9 | 8 | 9 | 9 | 4 |
| 36 | 1 | Pre | 0 | — | 0 | 0 | — | 2 | 0 | — | 0 | — |
| | | Post | — | 9 | 8 | 7 | 1 | 9 | 9 | 9 | 9 | 5 |
| 50 | 1 | Pre | 0 | — | 0 | 0 | — | 0 | 0 | 0 | 0 | 0 |
| | | Post | — | 0 | 0 | 0 | 0 | 0 | 0 | 0 | 0 | 0 |
| 51 | 1 | Pre | 0 | — | 0 | 0 | — | 0 | 0 | 0 | 0 | 0 |
| | | Post | — | 0 | 0 | 0 | 0 | 0 | 0 | 0 | 0 | 0 |
| 52 | 1 | Pre | 0 | — | 2 | 0 | — | 0 | — | 0 | 0 | 0 |
| | | Post | — | 0 | 0 | 3 | 0 | 2 | 3 | 0 | 0 | 0 |
| 53 | 1 | Pre | 0 | — | 5 | 6 | — | 6 | 9 | 9 | 6 | 2 |
| | | Post | — | 7 | 5 | 5 | 3 | 8 | 5 | 8 | 5 | 0 |
| 54 | 0.25 | Pre | 0 | — | 9 | 0 | — | 0 | 0 | 0 | 0 | 0 |
| | | Post | — | 0 | 0 | 0 | 0 | 0 | 5 | 1 | 0 | 0 |

TABLE VI

| Abbreviations used for Test Plants | |
|---|---|
| Sb - | Sugar Beet |
| Rp - | Rape |
| Ct - | Cotton |
| Sy - | Soybean |
| Mz - | Maize |
| Ww - | Winter wheat |
| Rc - | Rice |
| Bd - | *Bidens pilosa* |
| Ip - | *Ipomoea lacunosa* (pre-emergence) *Ipomoea hederacea* (post-emergence) |
| Am - | *Amaranthus retroflexus* |
| Pi - | *Polygonum aviculare* |
| Ca - | *Chenopodium album* |
| Ga - | *Galium aparine* |
| Xa - | *Xanthium spinosum* |
| Xs - | *Xanthium strumarium* |
| Ab - | *Abutilon theophrasti* |
| Eh - | *Euphorbia heterophylla* |
| Av - | *Avena fatua* |
| Dg - | *Digitaria sanguinalis* |
| Al - | *Alopecurus myosuroides* |
| St - | *Setaria viridis* |
| Ec - | *Echinochloa crus-galli* |
| Sh - | *Sorghum halepense* |
| Ag - | *Agropyron repens* |
| Ce - | *Cyperus esculentus* |

I claim:

1. A compound of formula (I) :

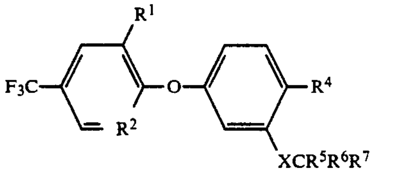

(I)

wherein

X is O, $S(O)_n$ or $NR^a$ where $R^a$ is H or alkyl and n is 0, 1 or 2;

$R^1$ is H or halo;

$R^2$ is N or $CR^3$ where $R^3$ is halo or $NO_2$;

$R^4$ is H, halo, $NO_2$, alkyl, haloalkyl, CN,$CO_2$alkyl, cycloalkyl, phenyl, COalkyl, COphenyl, CHO-,OH, $NH_2$, NHCOalkyl, or alkoxy;

$R^5$ is H, halo or optionally substituted alkyl;

$R^6$ is H, halo or optionally substituted alkyl provided that at least one of $R^5$ or $R^6$ is halo;

$R^7$ is CN, CHO, $COOR^8$, $CONR^8R^9$, where $R^8$ is H, optionally substituted alkyl, alkenyl, alkynyl or aryl and $R^9$ is a group $R^8$, $SO_2alkylNR^{10}R^{11}$ or $N^+R^{10}R^{11}R^{12}$ $Z^-$ where Z is an agriculturally acceptable anion and $R^{10}$, $R^{11}$ and $R^{12}$ are independently selected from hydrogen and alkyl.

2. A compound of formula (I) according to claim 1 wherein $R^1$ is F and $R^2$ is C—Cl.

3. A compound of formula (I) according to claims 1 or 2 where $R^4$ is H, Br, Cl, CN, $NO_2$.

4. A compound of formula (I) according to claims 1, 2 or 3 where $XCR^5R^6R^7$ is

F
|
$OCHCOOR^8$.

5. A process for preparing a compound of formula (I) as defined in claim (I) which comprises reacting a compound of formula (II):

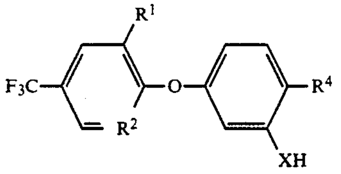

(II)

wherein $R^1$, $R^2$, $R^4$ and X are as defined for formula (I) in claim 1 with a compound of formula (III)

$Y—CR^5R^6R^7$ wherein $R^5$, $R^6$, $R^7$ are as defined for formula (I) in claim 1 and Y is a leaving group, and thereafter if desired carrying out one or more of the following steps:

i) when $R^7$ is alkoxycarbonyl hydrolysing to the corresponding acid; and ii) when $R^7$ is COOH esterifying or forming a salt, amide, sulphonamide, hydrazide or hydrazinium derivative;

6. A herbicidal composition comprising a compound of formula (I) as defined in claim 1 in combination with an agriculturally acceptable diluent or carrier.

7. A method of killing or controlling unwanted plants which method comprises applying to the plant or to a locus thereof, an herbicidally effective amount of a compound of formula (I) as defined in claim 1.

8. A compound of formula (I) according to claims 1, 2 or 3 where $R^8$ is $C_1$-$C_6$ alkyl.

9. A compound of formula (I):

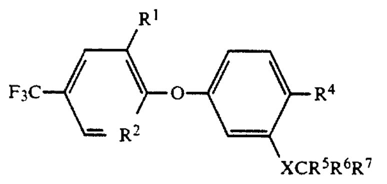

wherein

X is O;

$R^1$ is H or halo;

$R^2$ is $CR^3$ where $R^3$ is halo or $NO_2$;

$R^4$ is H, halo, $NO_2$, CN, CHO, alkyl, $CO_2$alkyl, COalkyl or cycloalkyl where alkyl has 1 to 6 carbon atoms;

$R^5$ is H, halo or alkyl having 1 to 6 carbon atoms;

$R^6$ is H or halo provided that at least one of $R^5$ or $R^6$ is halo;

$R^7$ is CHO, $COOR^8$ or $CONR^8R^9$;

where $R^8$ is H, alkyl, substituted alkyl, aryl or alkynyl where alkyl has 1 to 6 carbon atoms and $R^9$ is a group $R^8$ or $SO_2$ alkyl.

10. A compound of formula (I) according to claim 9 where $R^1$ is F and $R^3$ is halo or $NO_2$.

11. A compound of formula (I) according to claim 10 where $R^4$ is halo.

12. A compound of formula (I) according to claim 11 where $R^4$ is Cl.

13. A compound of formula (I) according to claim 11 where $R_3$ and $R_4$ are both chloro.

14. A compound of formula (I) according to claim 11 where $R^3$ is Cl or F.

15. A compound of formula (I) according to claims 12 or 14 where $R^7$ is $COOR^8$.

16. A compound of formula (I) according to claim 10 where $R^5$ is H and $R^6$ is F.

17. A compound of formula (I) according to claim 9 where $R^4$ is halo.

18. A compound of formula (I) according to claim 9 where $R_3$ and $R_4$ are both chloro.

19. A compound of formula (I) according to claim 9 where $R^5$ is H and $R^6$ is F.

20. A compound of formula (I) according to claim 17 where $R^5$ is H and $R^6$ is F.

21. A compound of formula (I) according to claim 9 where $R^7$ is $COOR^8$.

22. A compound of formula (I) according to claim 17 where $R^5$ is H, $R^6$ is F and $R^7$ is $COOR^8$.

23. A compound of formula (I) according to claims 9, 20 or 22 where $R^8$ is alkyl having 1 to 6 carbon atoms.

* * * * *